(12) United States Patent
Chen et al.

(10) Patent No.: US 8,734,697 B2
(45) Date of Patent: May 27, 2014

(54) PATCH PRODUCTION

(75) Inventors: Xianfeng Chen, Hong Kong (CN); Mark Anthony Fernance Kendall, Chelmer (AU); Tarl Prow, Annerley (AU); Anthony Paul Raphael, Coorparoo (AU)

(73) Assignee: The University of Queensland, St. Lucia (AU)

( * ) Notice: Subject to any disclaimer, the term of this patent is extended or adjusted under 35 U.S.C. 154(b) by 0 days.

(21) Appl. No.: 13/141,667

(22) PCT Filed: Dec. 17, 2009

(86) PCT No.: PCT/AU2009/001646
§ 371 (c)(1),
(2), (4) Date: Sep. 12, 2011

(87) PCT Pub. No.: WO2010/071918
PCT Pub. Date: Jul. 1, 2010

(65) Prior Publication Data
US 2012/0027810 A1    Feb. 2, 2012

(30) Foreign Application Priority Data
Dec. 22, 2008  (AU) ............................... 2008906580

(51) Int. Cl.
B29C 33/42    (2006.01)
(52) U.S. Cl.
USPC .......................................... 264/219; 264/220
(58) Field of Classification Search
USPC ................................................. 264/219, 220
See application file for complete search history.

(56) References Cited

U.S. PATENT DOCUMENTS

| | | | |
|---|---|---|---|
| 4,702,799 A | 10/1987 | Tuot | |
| 5,499,474 A | 3/1996 | Knooihuizen | |
| 5,859,937 A | 1/1999 | Nomura | |
| 5,922,356 A | 7/1999 | Koseki et al. | |
| 6,287,556 B1 | 9/2001 | Portnoy et al. | |
| 6,334,856 B1 | 1/2002 | Allen et al. | |
| 6,454,755 B1 | 9/2002 | Godshall | |
| 6,558,361 B1 | 5/2003 | Yeshurun | |
| 6,945,952 B2 | 9/2005 | Kwon | |
| 7,211,062 B2 | 5/2007 | Kwon | |
| 7,250,037 B2 | 7/2007 | Shermer et al. | |
| 8,052,633 B2 | 11/2011 | Kendall | |
| 2002/0128599 A1 | 9/2002 | Cormier et al. | |
| 2002/0177839 A1 | 11/2002 | Cormier et al. | |
| 2005/0042866 A1 | 2/2005 | Klapproth et al. | |
| 2005/0143713 A1 | 6/2005 | Delmore et al. | |
| 2005/0261632 A1 | 11/2005 | Xu | |
| 2006/0074376 A1 | 4/2006 | Kwon | |
| 2007/0060867 A1 | 3/2007 | Xu | |
| 2007/0078376 A1 | 4/2007 | Smith | |
| 2007/0224252 A1 | 9/2007 | Trautman et al. | |
| 2007/0270738 A1 | 11/2007 | Wu et al. | |
| 2007/0299388 A1 | 12/2007 | Chan et al. | |
| 2008/0108959 A1 | 5/2008 | Jung et al. | |

FOREIGN PATENT DOCUMENTS

| | | |
|---|---|---|
| EP | 0 139 286 A2 | 5/1985 |
| EP | 1 695 734 B1 | 6/2008 |
| WO | 91/06571 A1 | 5/1991 |
| WO | 94/24281 A1 | 10/1994 |
| WO | 99/02694 A1 | 1/1999 |
| WO | 99/42564 A2 | 8/1999 |
| WO | 99/64580 A1 | 12/1999 |
| WO | 00/05399 A1 | 2/2000 |
| WO | 00/42215 A1 | 7/2000 |
| WO | 00/74763 A2 | 12/2000 |
| WO | 01/33614 A1 | 5/2001 |
| WO | 01/85207 A2 | 11/2001 |
| WO | 02/064193 A2 | 8/2002 |
| WO | 02/075794 A2 | 9/2002 |
| WO | 03/026732 A2 | 4/2003 |
| WO | 03/092785 A1 | 11/2003 |
| WO | 2004/024224 A1 | 3/2004 |
| WO | 2005/060621 A2 | 7/2005 |
| WO | 2005/072630 A1 | 8/2005 |
| WO | 2006/101459 A1 | 9/2006 |
| WO | 2007/002123 A2 | 1/2007 |
| WO | 2007/030477 A2 | 3/2007 |
| WO | 2007/054090 A1 | 5/2007 |
| WO | 2007/061781 A1 | 5/2007 |
| WO | 2007/070004 A2 | 6/2007 |
| WO | 2007/080427 A2 | 7/2007 |
| WO | WO-2007/080427 A2 * | 7/2007 |

(Continued)

OTHER PUBLICATIONS

Aichele et al., "Antiviral Cytotoxic T Cell Response Induced by in Vivo Priming With a Free Synthetic Peptide," *Journal of Experimental Medicine* 171:1815-1820, May 1990.
Albert et al., "Dendritic cells acquire antigen from apoptotic cells and induce class I-restricted CTLs," *Nature* 392(6671):86-89, Mar. 1998.
Albert et al., "Tumor-specific killer cells in paraneoplastic cerebellar degeneration," *Nature Medicine* 4(11):1321-1324, Nov. 1998.
Athanasopoulos et al., "Gene therapy vectors based on adeno-associated virus: characteristics and applications to acquired and inherited diseases (Review)," *International Journal of Molecular Medicine* 6(4):363-375, Oct. 2000.
Bachmann et al., "Dendritic cells process exogenous viral proteins and virus-like particles for class I presentation to CD8.sup.+cytotoxic T lymphocytes," *European Journal of Immunology* 26(11):2595-2600, Nov. 1996.
Camilli et al., "*Listeria monocytogenes* Mutants Lacking Phosphatidylinositol-specific Phospholipase C Are Avirulent," *Journal of Experimental Medicine* 173:751-754, Mar. 1, 1991.

(Continued)

Primary Examiner — Ali Soroush
(74) Attorney, Agent, or Firm — Seed IP Law Group PLLC

(57) ABSTRACT

A method for use in producing a patch having a number of projections thereon. The method includes providing a distribution member and filling material on a mold surface, the mold including a number of cavities extending from the mold surface for defining the patch projections, filling the cavities with filling material, at least in part by urging filling material from the distribution member into the cavities, causing the filling material to solidify and separating the solidified filling material and the mold to thereby form the patch.

29 Claims, 30 Drawing Sheets

(56) References Cited

FOREIGN PATENT DOCUMENTS

| WO | 2007/127976 A2 | 11/2007 |
| WO | 2008/010681 A1 | 1/2008 |
| WO | 2008/011625 A2 | 1/2008 |
| WO | 2008/053481 A1 | 5/2008 |
| WO | 2008/069566 A1 | 6/2008 |
| WO | 2009/066763 A1 | 5/2009 |
| WO | 2009/097660 A1 | 8/2009 |
| WO | 2009/140735 A1 | 11/2009 |
| WO | 2010/109471 A1 | 9/2010 |

OTHER PUBLICATIONS

Cox et al., "Adjuvants—a classification and review of their modes of action," *Vaccine* 15(3):248-256, Feb. 1997.
Dreyer, "Microneedles: Microprocessing in medicine," Final Presentation, ENMA465 Project, URL=http://www.mse.umd.edu/undergrad/courses/ENMA465-project-results.html, May 10, 2004, 23 pages.
Gao et al., "Priming of influenza virus-specific cytotoxic T lymphocytes vivo by short synthetic peptides," *Journal of Immunology* 147(10):3268-3273, Nov. 1991.
Gardeniers et al., "Silicon micromachined hollow microneedles for transdermal liquid transport," *Journal of Microelectromechanical Systems* 12(6):855-860, Dec. 2003.
Gill et al., "Coated microneedles for transdermal delivery," *Journal of Controlled Release* 117(2):227-237, 2007.
Gill et al., "Coating formulations for Microneedles," *Pharmaceutical Research* 24(7):1369-1380, Jul. 7, 2007.
Ito et al., "Evaluation of self-dissolving needles containing low molecular weight heparin (LMWH) in rats," *International Journal of Pharmaceutics* 349(1-2):124-129, Feb. 12, 2008.
Ito et al., "Feasibility of microneedles for percutaneous absorption of insulin," *European Journal of Pharmaceutical Sciences* 29(1):82-88, Sep. 2006.
Ito et al., "Self-dissolving microneedles for the percutaneous absorption of EPO in mice," *Journal of Drug Targeting* 14(5):255-261, 2006.
Jondal et al., "MHC Class I—Restricted CTL Responses to Exogenous Antigens," *Immunity* 5(4):295-302, Oct. 1996.
Kay et al., "Viral vectors for gene therapy: the art of turning infectious agents into vehicles of therapeutics," *Nature Medicine* 7(1):33-40, Jan. 2001.
Kendall et al., "The mechanical properties of the skin epidermis in relation to targeted gene and drug delivery," *Biomaterials* 28(33): 4968-4977, Nov. 2007.
Kuzu et al., "In vivo priming effect during various stages of ontogeny of an influenza A virus nucleoprotein peptide," *European Journal of Immunology* 23(6):1397-1400, Jun. 1993.
Kwon, "Acne Treatment by a Dissolvable Micro-Needle Patch," Controlled Release Society 33rd Annual Meeting, 2006, 2 pages.
Kwon, *Controlled Release Society 34th Annual Meeting Transactions*, 2007. (Incorrectly cited on p. 2 of Spec. See: Oh et al., "Demonstration of Dose-controlled Delivery by Dissolvable Micro-needle Arrays," Controlled Release Society 34th Annual Meeting and Exposition Jun./Jul. 7-11, 2007, 2 pages).
Kwon, "In Vitro Evaluation of Transdermal Drug Delivery by a Micro-needle Patch," Abstract #115, Controlled Release Society 31st Annual Meeting Transactions, 2004, 2 pages.
Kwon, "In Vitro Modeling of Transdermal PTH Delivery by Dissolving Micro-needle Patch," TheraJect Web Site (2007), 2 pages.
Kwon, "Rapid Intradermal Drug Delivery by a Dissolvable Micro-Needle Patch," Abstract #306, Controlled Release Society 32nd Annual Meeting & Exposition Transactions, 2005, 2 pages.
Lee et al., "Dissolving microneedles for transdermal drug delivery," *Biomaterials* 29(13):2113-2124, May 2008.
Lin et al., "Silicon-processed microneedles," *IEEE Journal of Microelectromechanical Systems* 8(1):78-79, Mar. 1999.
Mengaud et al., "Expression in *Escherichia coli* and sequence analysis of the listeriolysin O determinant of *Listeria monocytogenes*," *Infection and Immunity* 56(4):766-772, Apr. 1988.
Miyano et al., "Hydrolyticmicroneedles as Transdermal Drug Delivery System," *International Solid-State Sensors, Actuators and Microsystems Conference Transducers 2007*, pp. 355-358, Jun. 10-14, 2007.
Miyano et al., "Sugar Micro Needles as Transdermic Drug Delivery System," *Biomedical Microdevices* 7(3):185-188, Sep. 2005.
Moore et al., "Introduction of soluble protein into the class I pathway of antigen processing and presentation," *Cell* 54(6):777-785, Sep. 9, 1988.
Oh et al., "Demonstration of Dose-controlled Delivery by Dissolvable Micro-needle Arrays," Controlled Release Society 34th Annual Meeting and Exposition Jun./Jul. 7-11, 2007, 2 pages. (Incorrectly cited on p. 2 of Spec as: Kwon, *Controlled Release Society 34th Annual Meeting Transactions*, 2007.)
Oh et al., "Intradermal influenza vaccine delivery using skin-penetrating dissolvable vaccine microneedles," AAPS Annual Meeting and Exposition, 2006, 1 page.
Palmer et al., "Streptolysin O: a proposed model of allosteric interaction between a pore-forming protein and its target lipid bilayer," *Biochemistry* 37(8):2378-2383, Feb. 1998.
Park et al., "Biodegradable polymer microneedles: Fabrication, mechanics and transdermal drug delivery," *Journal of Controlled Release* 104(1):51-66, May 5, 2005.
Park et al., "Polymer Microneedles for Controlled-Release Drug Delivery," *Pharmaceutical Research* 23(5):1008-1019, May 2006.
Portnoy et al., "Capacity of listeriolysin O, streptolysin O, and perfringolysin O to mediate growth of *Bacillus subtilis* within mammalian cells," *Infection and Immunity* 60(7):2710-2717, Jul. 1992.
Rossjohn et al., "Structure of a Cholesterol-Binding, Thiol-Activated Cytolysin and a Model of Its Membrane Form," *Cell* 89(5):685-692, May 30, 1997.
Schulz et al., "Peptide-induced antiviral protection by cytotoxic T cells," *Proceedings of the National Academy of Sciences USA* 88:991-993, Feb. 1991.
Silver et al., "Viscoelastic properties of young and old human dermis: A proposed molecular mechanism for elastic energy storage in collagen and elastin," *Journal of Applied Polymer Science* 86(8):1978-1985, Nov. 2002.
Stoeber et al., "Arrays of hollow out-of-plane microneedles for drug delivery," *Journal of Microelectromechanical Systems* 14(3):472-479, Jun. 2005.
Sullivan et al., "Minimally Invasive Protein Delivery with Rapidly Dissolving Polymer Microneedles," *Advanced Materials* 20(5):933-938, Mar. 2008.
Tao et al., "A systematic study of dry etch process for profile control of silicon tips," *Microelectronic Engineering* 78-79:147-151, Dec. 31, 2004.
Vigna et al., "Lentiviral vectors: excellent tools for experimental gene transfer and promising candidates for gene therapy," *Journal of Gene Medicine* 2(5):308-316, Sep./Oct. 2000.
Walther et al., "Viral Vectors for Gene Transfer: A Review of Their Use in the Treatment of Human Diseases," *Drugs* 60(2):249-271, Aug. 2000.
Wu et al., "Production of viral vectors for gene therapy applications," *Current Opinion in Biotechnology* 11(2):205-208, Apr. 2000.
Yuan et al., "Measuring microelastic properties of stratum corneum," *Colloids and Surfaces B: Biointerfaces* 48(1):6-12, Mar. 1, 2006.
Zhou et al., "Liposome-Mediated Cytoplasmic Delivery of Proteins: An Effective Means of Accessing the MHC Class I-Restricted Antigen Presentation Pathway," *Immunomethods* 4(3):229-235, Jun. 1994.

\* cited by examiner

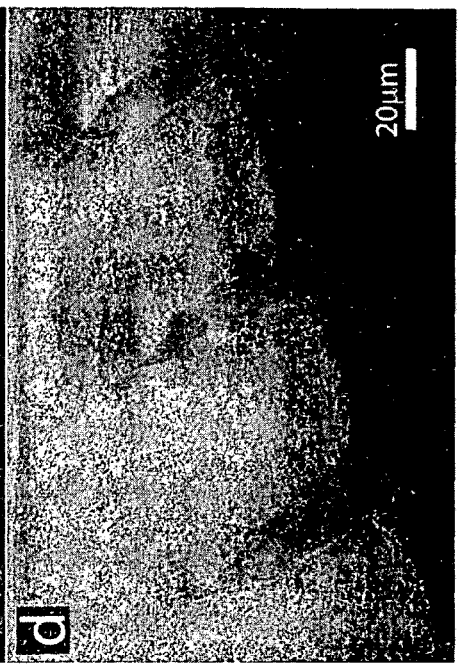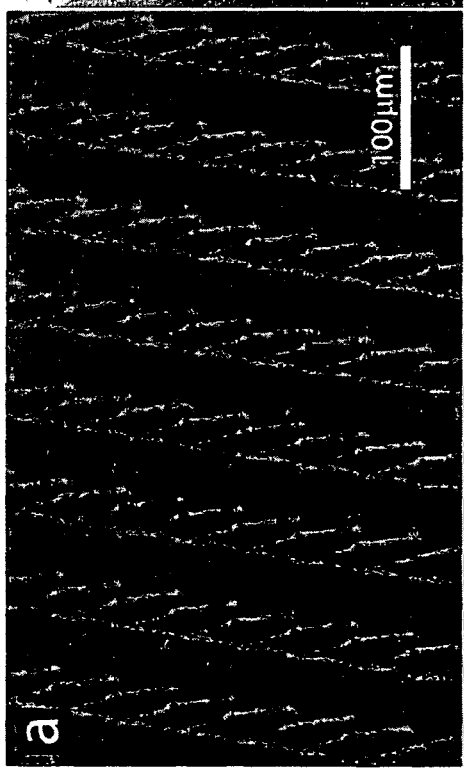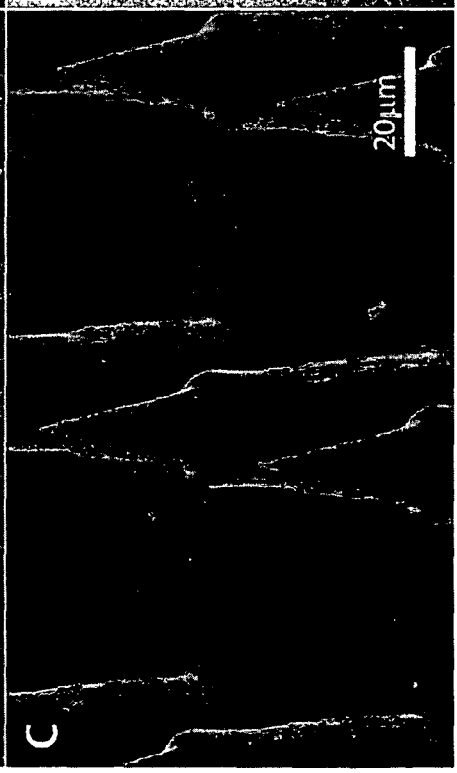

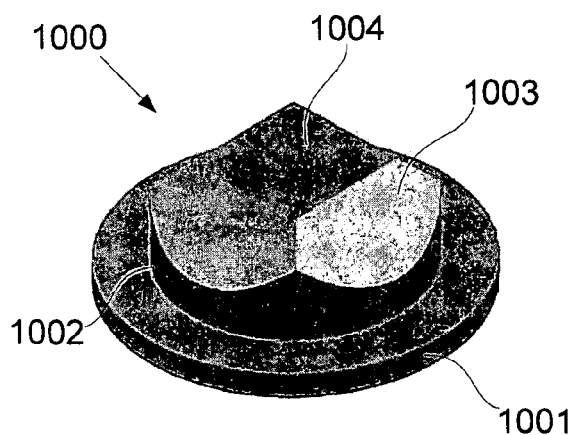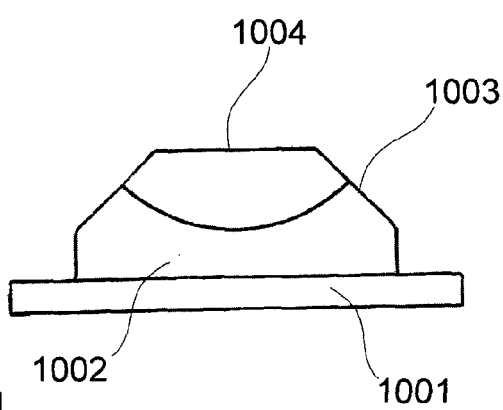
Fig. 10A          Fig. 10B
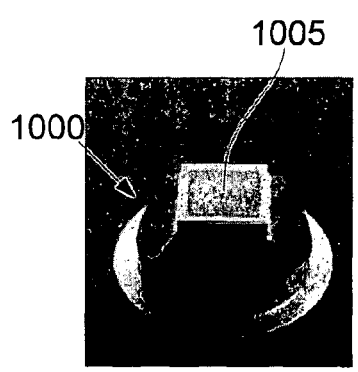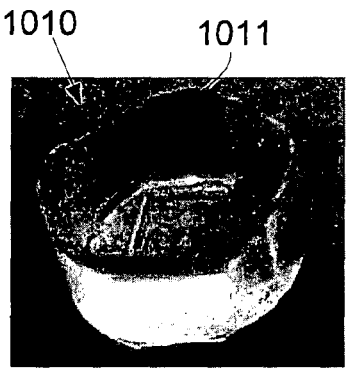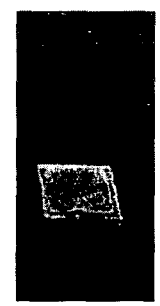
Fig. 10C          Fig. 10D          Fig. 10E

PATCH PRODUCTION

BACKGROUND OF THE INVENTION

The present invention relates to a method and apparatus for use in producing a patch having a number of projections thereon, and in particular to a method of producing a patch using a molding process.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

It is known to provide patches including a number of projections thereon to allow bioactive material to be administered to a subject. Such arrays of projections or needles on a patch are an increasingly effective way of delivering therapeutic agents or biomarkers since there is minimal or no pain, little or no injury from the needle and highly reduced possibility of cross infection. The solid projections or needles on a patch can be made of multiple layers of drugs, macromolecules or nanoparticles alone or with structural excipient(s). These devices can be subsequently delivered to a desired target by the penetration of the projections or needles into the skin.

For example, WO2005/072630 describes devices for delivering bioactive materials and other stimuli to living cells, methods of produce of the device and various uses of the device, including a number of medical applications. The device comprises a plurality of projections which can penetrate a body surface so as to deliver the bioactive material or stimulus to the required site. The projections are typically solid and the delivery end section of the projection is so dimensioned as to be capable of insertion into targeted cells to deliver the bioactive material or stimulus without appreciable damage to the targeted cells or specific sites therein.

Single needle devices can be composed of insoluble and/or dissolvable materials. For example, EP0139286 and U.S. Pat. No. 5,922,356 disclose a sustained-release single needle like device that is composed of a biocompatible and biodegradable carrier. The device was produced by mixing interferon with a number of structural excipients (i.e. collagen or gelatine) followed by compression molding. The compressed device was then subjected to lyophilisation or fixation with gluteraldehyde. An alternate method was also described wherein the payload was spray dried or lyophilised prior to compaction. However, the use of a single needle provides only limited opportunity for delivery of material to a subject.

WO2006/101459A1 describes a device with biodegradable needle tips. The device is composed of a microneedle array (length 100-150 um; diameter 10 um; 25 200 needles with spacing of 500 um). The microneedles are usually hollow or porous silicon. The payload is in liquid form that can be applied with or after the device has been applied, thereby limiting the ability to control the delivery location and amount of payload. The tips biodegrade in 2-3 weeks.

WO2008/010681A1, US-2008/0108959A1, and WO2008/069566A1 describe a difficult and time consuming method to generate dissolvable microneedles. The device is composed of PLA, CMC, and/or molten maltose. A surface is layered with viscous material. Small pillars are placed on top of the viscous material and slowly withdrawn to form threads. The threads are cut at the desired length. However, this is a prolonged and inconsistent method of producing the needles.

Various molding methods of making dissolvable microneedles are known. For example, the most utilized methodology described in the scientific literature is forcing a solution into a mold and drying (Ito et al. European Journal of Pharmaceutical Research, 29 (2006) 82-88; Ito et al. Journal of Drug Targeting, 14 (2006) 255-261; Ito et al. International Journal of Pharmaceutics, 349 (2008) 124-129; Sung-Yun Kwon, Controlled Release Society $31^{st}$ Annual Meeting Transactions (2004); Sung-Yun Kwon, Controlled Release Society $32^{nd}$ Annual Meeting Transactions (2005); Sung-Yun Kwon, TheraJect Web Site (2006); Oh et al. AAPS Annual Meeting and Esposition, (2006); Sung-Yun Kwon, Controlled Release Society $34^{nd}$ Annual Meeting Transactions (2007); Sung-Yun Kwon, TheraJect Web Site (2007); Lee et al. Biomaterials, 29 (2008) 2113-2124. The force used is generally mechanical or centrifugal. The agents usually used as excipients are sugars.

This methodology can only be compatible with biological materials if care is taken with temperature, chemicals, etc, which is difficult in many cases. Additionally, these techniques can only generally be used to provide single layer needles, thereby limiting delivery of material to subjects.

Kwon CRS 2007 describes layering of needles by producing a single layer containing polystyrene microparticles that were concentrated in the tips of microneedles by centrifugation. This methodology is similar to that described in WO2007/030477A2, in which the drug is made as a particulate or is adsorbed onto a particulate material. These particulates are then concentrated towards the tips of microneedle arrays (length 100-3000 um, diameter 1-2000 um) during a casting process. However, as the payload must be in a particulate form to be used a large gradient is associated with this method, preventing layers being formed at a micron scale. This limits the ability of the device to selectively deliver material to a subject. Additionally, although a layer is formed in the sense that particles are only provided near projection tips, the particles are still suspended in the same material as used to make the projections, meaning that the underlying material will be delivered along the entire length of the needle.

Another common methodology used to create dissolving microneedles is by casting molten materials, usually sugars (Miyano et al. Biomedical Microdevices, 7 (2005) 185-188; Miyano et al. IEEE Transcripts, 10-14 (2007) 355-358; Park et al. Journal of Controlled Release, 104 (2005) 51-66; Park et al. Pharmaceutical Research, 23 (2006) 1008-1019; Sullivan et al. Advanced Materials, 20 (2008) 933-938.) These reports detail the production of dissolvable microneedles through heating the material from 37 C to 140 C. These methodologies are not compatible with most biological and some chemical payloads, and again do not describe or allow layering, thereby limiting the ability to control payload delivery to the subject.

Park et al. Pharmaceutical Research, 23 (2006) 1008-1019, describes a layering process similar to that of WO2007/127976A2 in which dissolvable microneedles (length 600 um) are formed using microparticles. The microparticles are composed of PLA, PGA, and PLGA copolymers and are forced into a female mold where the microparticles are welded together using chemical, ultrasonic energy, or heat methodologies. Dual-layering is achieved by forcing particles into the mold and melting followed by the addition of different particles with lower melting points than the previous layer.

However, the quality of these techniques can be poor as there are significant (>50 um) gradients formed by the best of the layering methods. Additionally, none of the patents, patent applications, nor publications describe a methodology to accurately deposit multiple layers of different compositions at a micrometer scale.

WO2004/024224A1 describes the method of produce of a microperforator. This device is made of a solidifiable material mixed with a diagnostic or therapeutic agent. The device is meant to be porous so as to allow payload release. The device can be implemented in either single or multiple microperforators. The microperforator is insoluble in the skin. The casting method utilizes a master mold into which sol/gel containing silicate is cast. The payload is mixed with methanol and heated to 60 C. The material is then physically compressed and dried at 60-100 C. This process makes the use of biological agents impossible and seriously limits the use of drugs.

U.S. Pat. No. 6,945,952B2 and U.S. Pat. No. 7,211,062B2 describe a dissolving microneedle array (length 100-1000 um, diameter 1-1000 um, and 20-200 microneedles per square cm). The dissolving microneedles are cast from carbohydrates using centrifugal force. Polymer needles are also described and require uv photo-cross linking. Powder can also be forced into mold with heat. However, again this does not describe or allow layering and the use of heat limits the ability to use bioactive materials.

Previous systems have also focussed on generating large and very sparsely packed projections. Such techniques often prove to be unsuccessful when making small and densely packed projections. No technologies are sufficiently capable of generating multiple layered needles from the nanometer to millimeter scales.

Additionally, the systems described above provide only limited mechanisms to deliver multiple payloads to the subject, with very little control over delivery of material to specific strata within the skin and no mechanisms to separate incompatible payloads. Furthermore there is little ability to control the release of payload from the resulting patches.

For successful vaccine delivery systems, effective layering of vaccines and adjuvants in the patch projections in a controlled manner, followed by the rapid, subsequent release of an effective amount of the vaccine in the skin, in a strata dependant manner, after application of the patch, is required. Further, whilst it is desirable to employ patches that have smaller projections or needles, effectively generating these using existing techniques is difficult.

Thus, current techniques are only able to produce functional dissolving microneedles on a large scale—600 µm to 3.24 mm. Attempts at producing dissolving microneedles that consist of multiple layers, involve harsh chemical processes, which rely on polymer melts. These microneedles are suitable at delivering drugs, however they are limited in protein and DNA delivery.

Success has been achieved in producing dual layer systems under physiological conditions. Microneedles are filled with one active solution followed by removal of excess solution. A backing layer is then applied and the microneedles are dried. This method is limited to two layers and for a sufficient amount of active in the backing layer to diffuse into the skin a long application time would be required.

SUMMARY OF THE PRESENT INVENTION

The present invention seeks to substantially overcome, or at least ameliorate, one or more disadvantages of existing arrangements.

In a first broad form the present invention provides a method for use in producing a patch having a number of projections thereon, the method including:
  a) providing a distribution member and filling material on a mold surface, the mold including a number of cavities extending from the mold surface for defining the patch projections;
  b) filling the cavities with filling material, at least in part by urging filling material from the distribution member into the cavities;
  c) causing the filling material to solidify; and,
  d) separating the solidified filling material and the mold to thereby form the patch.

Typically the method includes causing filling material on the mold surface to solidify, thereby forming a patch base.

Typically the method includes:
  a) providing the distribution member on the mold surface; and,
  b) applying the filling material to the distribution member.

Typically the distribution member is at least one of:
  a) a diffusion filter; and,
  b) a membrane.

Typically the method of solidifying the filling material includes at least one of:
  a) exposure to vacuum;
  b) temperature control;
  c) humidity control;
  d) using a gas flow;
  e) exposing the filling material to a reagent;
  f) exposing the filling material to UV light; and,
  g) exposing the filling material to radiation.

Typically the method of urging the filling material into the cavities includes using a centrifuge.

Typically the method includes:
  a) calculating a volume of filling material required to at least partially fill the cavities; and,
  b) filling the cavities using the calculated volume of filling material.

Typically the method includes forming the projections with at least two layers of filling material.

Typically resulting projections include at least two layers.

Typically the method includes, filling the cavities with filling material by:
  a) partially filling the cavities with a first filling material; and,
  b) filling the cavity using at least a second filling material.

Typically the method includes filling the cavity using at least a third filling material.

Typically the third filling material at forms the patch base.

Typically the method includes:
  a) determining a layer depth;
  b) calculating a volume of first fluid material in accordance with the layer depth; and,
  c) filling the cavities using the calculated volume of first fluid.

Typically the method includes:
  a) urging first filling material from a first distribution member into the cavities, to thereby partially fill the cavities;
  b) causing the first filling material to solidify;
  c) urging second filling material from a second distribution member into the cavities, to thereby fill the cavities; and,
  d) causing the second filling material to solidify.

Typically the method includes:
  a) urging third filling material from a third distribution member into the cavities, to thereby fill the cavities; and,
  b) causing the third filling material to solidify.

Typically the method includes replacing the first distribution member with the second distribution member prior to providing the second filling material.

Typically the method includes:
a) determining mold properties; and,
b) selecting filling material properties at least partially in accordance with the mold properties.

Typically the mold properties include at least one of:
a) cavity size;
b) cavity shape;
c) cavity spacing;
d) cavity surface properties; and,
e) mold materials.

Typically the filling material properties include at least one of:
a) a surface tension; and,
b) a viscosity.

Typically the method includes forming a filling material having selected filling material properties, the filling material including at least one of:
a) a viscosity enhancer;
b) a detergent;
c) a surfactant; and,
d) an adjuvant.

Typically the filling material is dissolvable on contact with fluid in a subject.

Typically the filling material includes a material for delivery to a subject in use.

Typically the material is at least one of:
a) a biological agent; and,
b) a therapeutic agent.

Typically the material is at least one of.
a) nanoparticles;
b) a nucleic acid or protein;
c) an antigen, allergen, or adjuvant;
d) parasites, bacteria, viruses, or virus-like particles;
e) quantum dots, SERS tags, raman tags or other nanobiosensors;
f) metals or metallic compounds;
g) molecules, elements or compounds;
h) DNA;
i) protein;
j) RNA, siRNA, sfRNA, iRNA;
k) synthetic biological materials;
l) polymers; and,
m) drugs.

Typically the method includes:
a) creating a male mold having a number of projections;
b) using the male mold to thereby form the mold.

Typically the method includes creating the male mold using an etching process.

Typically the method includes etching a silicon substrate to thereby form the male mold.

In a second broad form the present invention provides apparatus for use in producing a patch having a number of projections thereon, the apparatus including:
a) a mold including a number of cavities extending from the mold surface for defining patch projections; and,
b) a distribution member positioned on a mold surface, the distribution member including a filling material, wherein in use:
  i) filling material is urged from the distribution member into the cavities;
  ii) the filling material is solidified; and,
  iii) the solidified filling material and the mold are separated to thereby form the patch.

In a third broad form the present invention seeks to provide a method for use in producing a patch having a number of projections thereon, the method including:
a) providing first filling material on a mold surface, the mold including a number of cavities extending from the mold surface for defining the patch projections;
b) partially filling the cavities with first filling material;
c) causing the first filling material to solidify;
d) providing second filling material on the mold surface;
e) filling the cavities with second filling material;
f) causing the second filling material to solidify; and,
g) separating the solidified filling material and the mold to thereby form the patch.

Typically the method includes:
a) providing a distribution member on the mold surface; and,
b) at least partially filling the cavities with filling material, at least in part by urging filling material from the distribution member into the cavities.

In a fourth broad form the present invention seeks to provide a patch for delivering material to a subject, the patch including:
a) a substrate; and,
b) a number of projections provided on the substrate, the projections including the material and being dissolvable on contact with fluid in a subject to thereby deliver the material to the subject.

Typically the projections include at least one layer containing the material.

Typically the at least one layer is arranged to deliver material to a region of interest within the subject.

BRIEF DESCRIPTION OF THE DRAWINGS

An example of the present invention will now be described with reference to the accompanying drawings, in which:—

FIGS. 9A and 9C are SEM images of an example of a male mold;

FIGS. 9B and 9D are SEM images of an example of a female mold;

FIGS. 10A and 10B are schematic diagrams of an example of a support for supporting a male mold during casting of a female mold;

FIG. 10C is an image of an example of a support for supporting a male mold during casting of a female mold;

FIG. 10D is an image of an example of a female mold;

FIG. 10E is an image of an example of a fabricated projection patch;

DETAILED DESCRIPTION OF THE PREFERRED EMBODIMENTS

An example of a device for delivering material to targets within a body will now be described with reference to FIGS. 1A to 1F.

In this example, the device is in the form of patch 100 having a number of projections 110 provided on a surface 121 of a substrate 120. The projections 110 and substrate 120 may be formed from any suitable material, but in one example, are formed from a silicon type material. The projections may be solid, non-porous and non-hollow, although this is not essential.

In the example shown, the patch has a width W and a breadth B with the projections 110 being separated by spacing S.

Figure 1A:
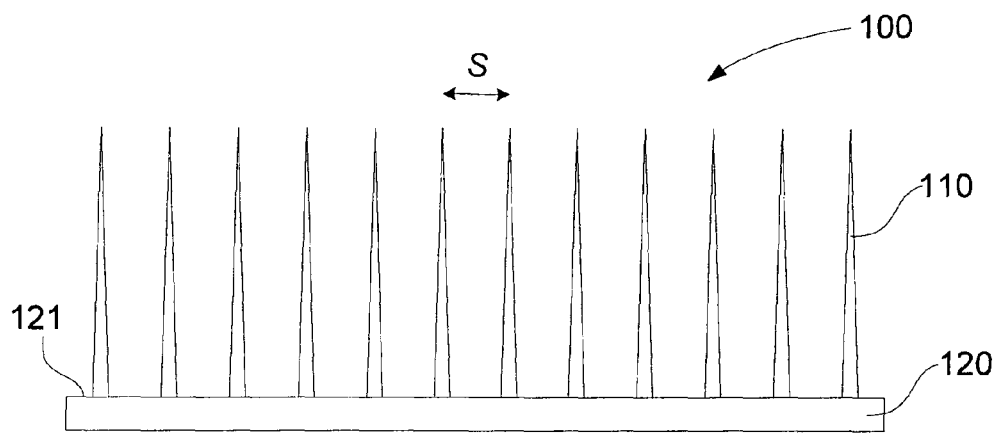
FIGS. 1A and 1B are schematic side and plan views of an example of device for delivery of material to targets within a body.
Figure 1B:
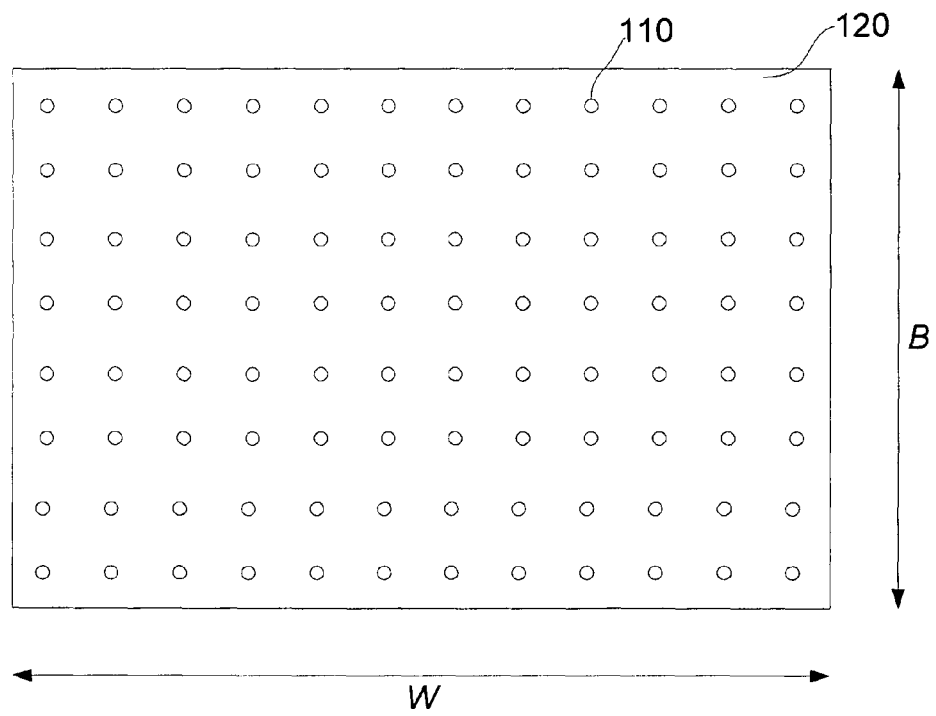
Figure 1C:
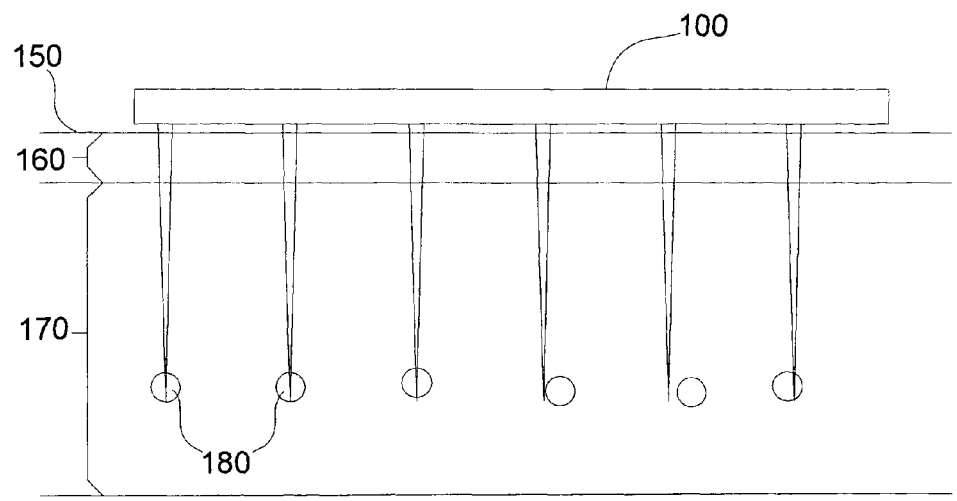
FIG. 1C is a schematic diagram of an example of the device of FIG. 1A in use.

In use, the patch 100 is positioned against a surface of a subject, allowing the projections to enter the surface and provide material to targets therein. An example of this is shown in FIG. 1C.

In this example, the patch 100 is urged against a subject's skin shown generally at 150, so that the projections 110 pierce the Stratum Corneum 160, and enter the Viable Epidermis 170 to reach targets of interest, shown generally at 180. However, this is not essential and the patch can be used to deliver material to any part or region in the subject.

Figures 1D, 1E, 1F:
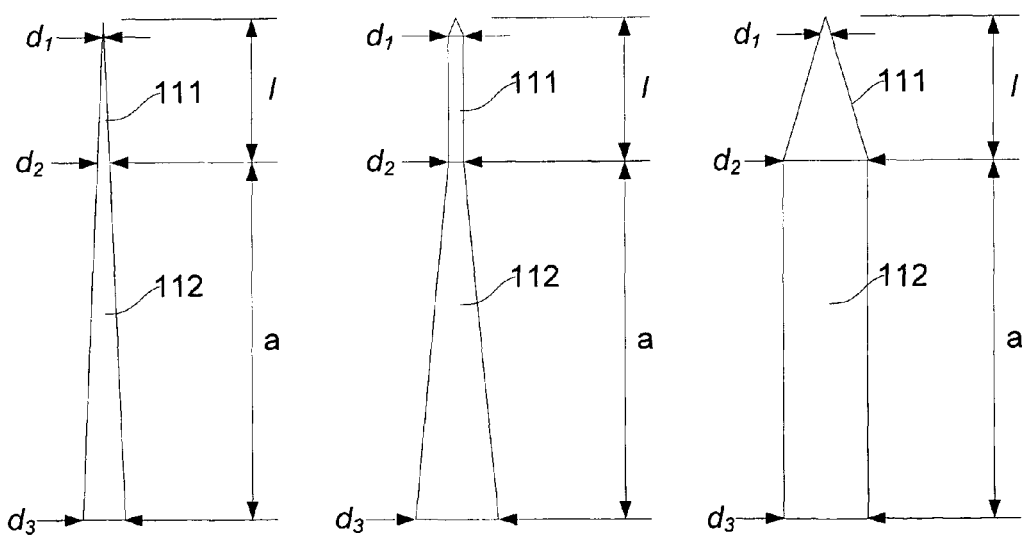
FIGS. 1D to 1F are schematic diagrams of examples of projections used in the device of FIG. 1A.
Figure 2:
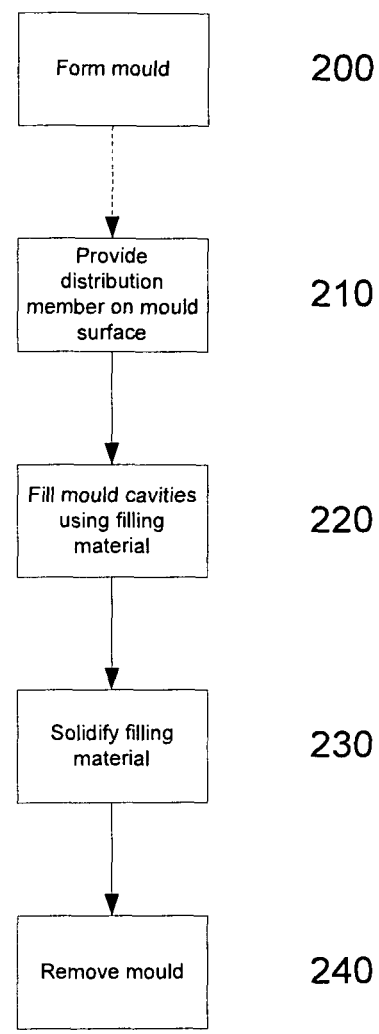
FIG. 2 is a flow chart of an example of an example of a patch production process.

It will be appreciated that the projections can have a variety of shapes, and examples of suitable projection shapes are shown in more detail in FIGS. 1D, 1E and 1F.

In one example, the projection includes a targeting section 111, intended to deliver the material or stimulus to targets within the body, and a support section 112 for supporting the targeting section 111. However, this is not essential, and a single element may be used. In the example of FIG. 1D, the projection is formed from a conically shaped member, which tapers gradually along its entire length. In this example, the targeting section 111 is therefore defined to be the part of the projection having a diameter of less than $d_2$.

In FIGS. 1E and 1F, the structure of the projection may vary along its length to provide a defined targeting section 111 with a designed structure. In the example of FIG. 1E, the targeting section 111 is in the form of a substantially cylindrical shape, such that the diameter $d_1$ is approximately equal to the diameter $d_2$, with a tapered support section, such that the diameter $d_2$ is smaller than the diameter $d_3$. In contrast, in the example of FIG. 1F, the targeting section 111 is in the form of taper such that the diameter $d_1$ is smaller than the diameter $d_2$, with a cylindrical support section, such that the diameter $d_2$ is substantially equal to the diameter $d_3$.

In general, the support section 112 has a length a, whilst the targeting section 111 has a length l. The diameter of the tip is indicated by $d_1$, whilst the diameter of the support section base is given by $d_3$.

In use, the device can be used to deliver material to specific targets within the body or more generally to the blood supply, or tissue within the body and the configuration of the device will tend to depend on its intended use.

Thus, for example, if the patch is configured so as to ensure material is delivered to specific targets such as cells, then it may be necessary to select a more specific arrangement of projections than if delivery is provided more generally to the blood. To achieve this, the device can be provided with a particular configuration of patch parameters to ensure specific targeting. The patch parameters can include the number of projections N, the spacing S between projections, and the projection size and shape. This is described in more detail in co-pending application U.S. Ser. No. 11/496,053.

In one specific example, a patch having a surface area of approximately 0.16 cm$^2$ has projections provided at a density of between 1,000-30,000 projections/cm$^2$, and typically at a density of approximately 20,000 projections/cm$^2$. However, alternative dimensions can be used. For example, a patch for an animal such as a mouse may have a surface area of 0.32 to 0.48 cm$^2$, whereas as a patch for a human may have a surface area of approximately 1 cm$^2$. A variety of surface areas can be achieved by mounting a suitable number and arrangement of patches on a common substrate.

The projections typically have a length of between 10 μm to 5 mm and typically 90 μm for mouse and 200-500 μm for human with a radius of curvature of greater than 1 μm and more typically greater than 5 μm. However, it will be appreciated that other dimensions may be used.

If distinct targeting section and support sections are provided, the targeting section typically has a diameter of less than 1 μm and more typically less than 0.5 μm. The length of the targeting section is typically less than 100 μm, less than 10 μm and typically less than 5 μm. The length of the support section typically varies depending on the location of the target within the subject. Example lengths include less than 200 μm for epidermal delivery, less than 1000 μm for dermal cell delivery, 600-800 μm for delivery to basal cells in the epithelium of the mucosa and approximately 100 μm for lung delivery.

An example of a patch production process will now be described with reference to FIGS. 2 and 3A to 3D.

In this example, at step 200 a mold is typically formed. It will be appreciated that the mold need only be formed a single time to allow multiple patches to be produced and that a number of different molds may be used to allow patches having different configurations to be produced.

Figure 3A:
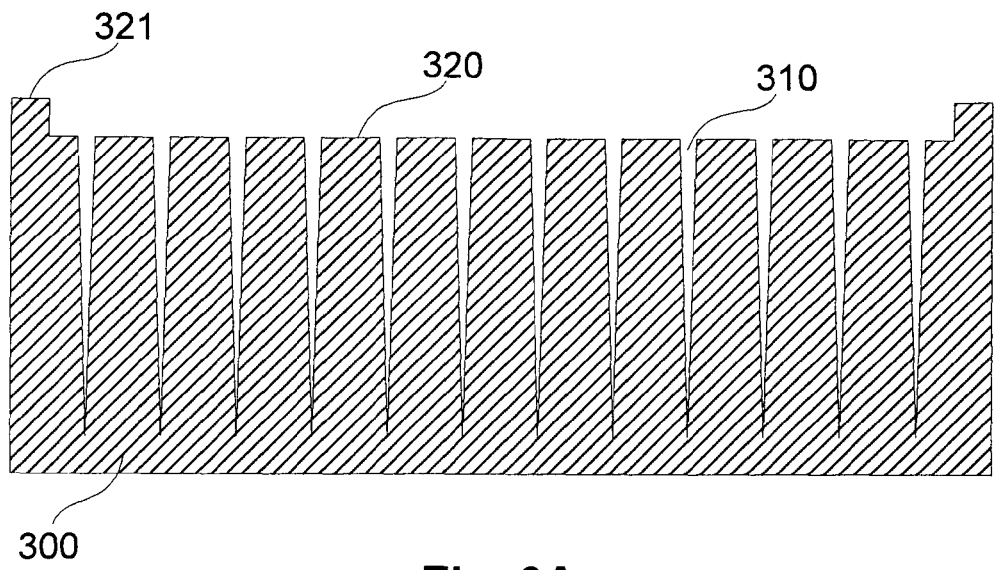
FIGS. 3A to 3D are schematic diagrams of the steps in the patch production process of FIG. 2.
Figure 3B:
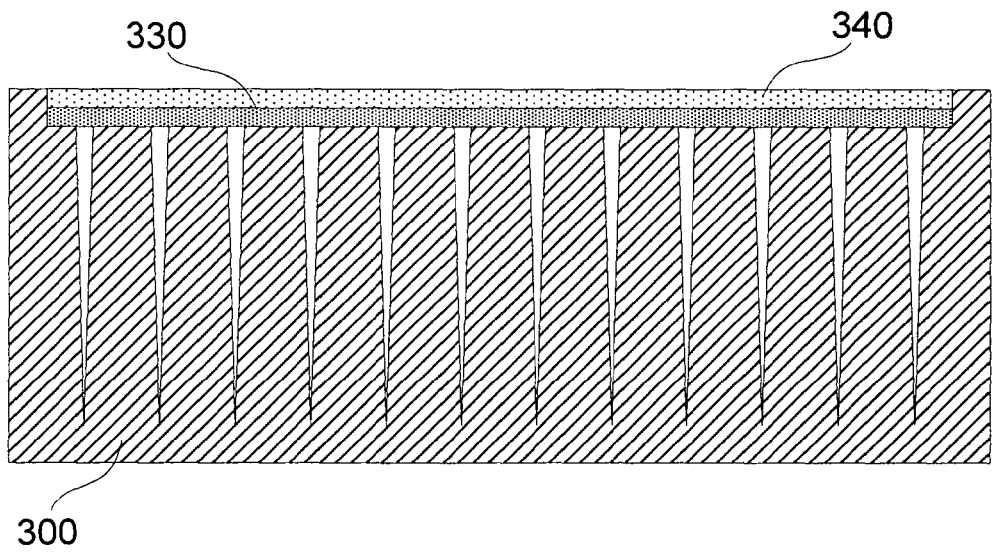

The mold is typically a female mold, an example of which is shown in FIG. 3A. In this example, the mold includes a body 300 having a number of cavities 310 extending from a surface 320. The mold surface 320 may also include a raised perimeter edge 321 The mold may be produced in any suitable manner, but in one example is produced using a male mold, that is an inverse of the female mold, as will be described in more detail below. In this example the mold is formed from a polymer such as PDMS (Polydimethylsiloxane), although any suitable material may be used.

At step 210 a distribution member 330 is provided on the mold surface 320, together with a filling material 340. The distribution member 330 may be any form of suitable member that is capable of allowing distribution of the filling material 340 to each of the cavities 310. In one example, the distribution member is therefore formed from a permeable material, such as a diffusion filter, a polyethersulfone (PES) porous membrane, or the like, into which filling material may be provided.

The filling material may be provided within the distribution member using any suitable mechanism. Thus, in one example the distribution member 330 may be immersed in filling material prior to being provided on the mold surface 320. Alternatively however, the distribution member 330 can be provided on the mold surface 320, allowing the filling material 340 to be subsequently applied, for example in the form of a droplet or the like. This can be used to control the amount of material to be provided to each cavity, thereby allowing the cavities 310 to be filled to a predetermined depth, as will be described in more detail below.

Additionally, or alternatively, a larger volume of filling material than is required to fill the cavities may be provided. In this instance, filling material retained on the mold surface, either by the distribution member 330, or the ridge 321 and can be used to form the patch base 120.

Any suitable filling material may be used, and in one example the filling material is a solution containing a material such as an active compound and/or sugar-based excipient, such as carboxy-methylcellulose (CMC).

Figure 3C:
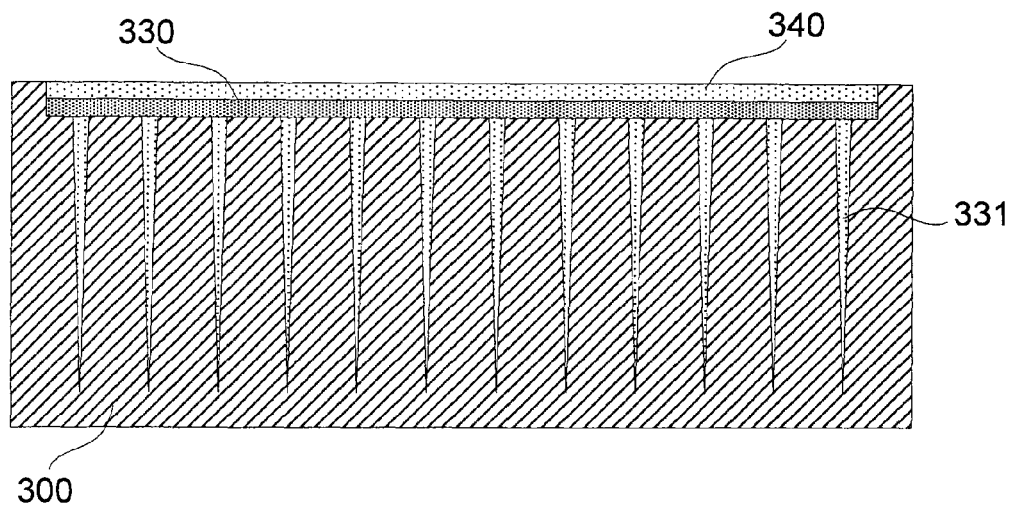

At step 220 the mold cavities 310 are filled using the filling material, as shown at 341 in FIG. 3C. This may be achieved in any suitable manner but typically involves urging the filling material into the cavities, for example using a centrifuge, or other similar technique.

At step 230 the filling material is solidified. The distribution member can be removed prior to solidification of the filling material, although this is not essential, and alternatively the distribution member may be incorporated into the patch base 120.

The manner in which solidification is performed will depend on the nature of the filling material. Thus, for example, the filling material may be adapted to solidify at room temperature, allowing solidification to occur naturally over time. This can be achieved through the use of a solvent that evaporates at room temperature, or a resin that cures at room temperature. However, alternative mechanisms for solidifying the material may be used, such as:
  exposure to vacuum;
  temperature control;
  humidity control;
  using a gas flow;
  exposing the filling material to a reagent;
  exposing the filling material to UV light; and,
  exposing the filling material to radiation, or any other energy source, such as microwave and infrared radiation.

Figure 3D:
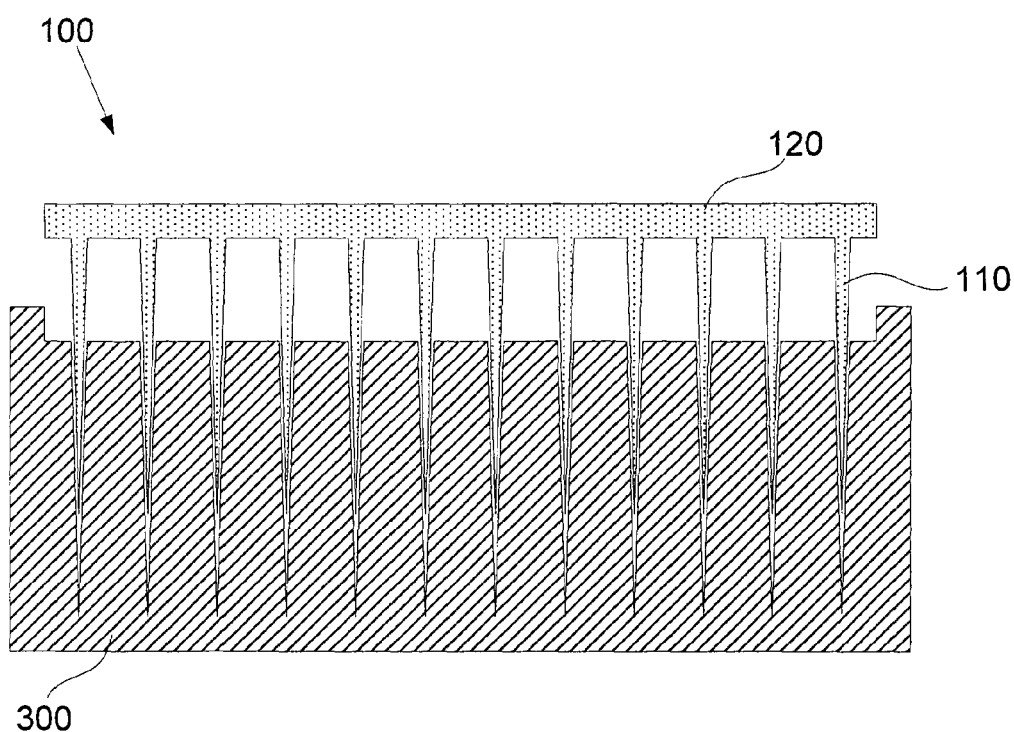
Figure 4A:
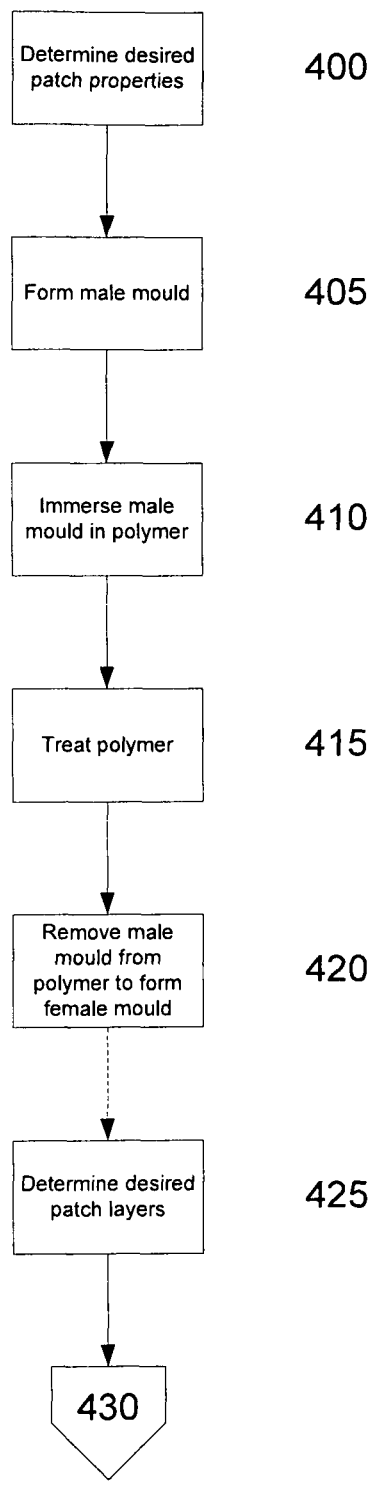
FIGS. 4A to 4C are a flow chart of an example patch production process.
Figure 4B:
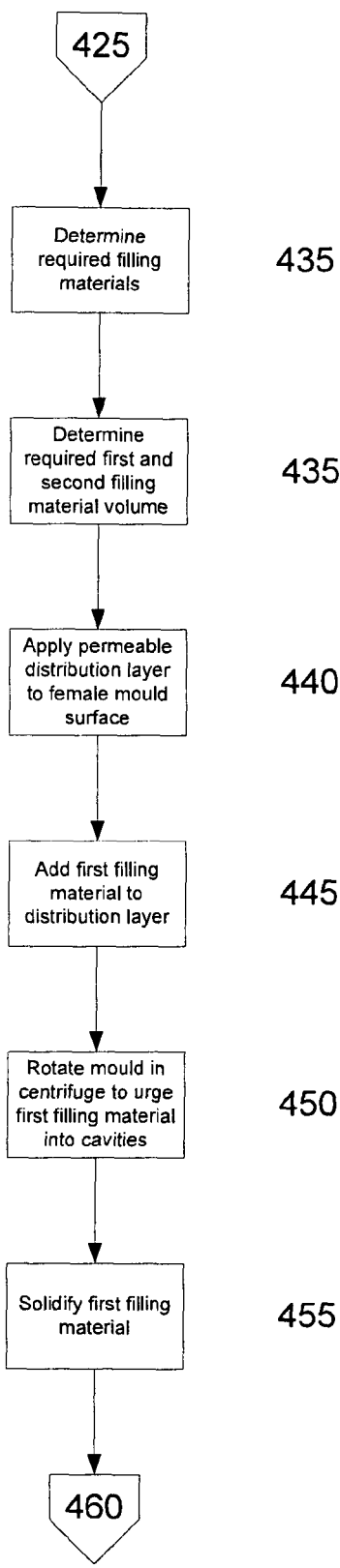
Figure 4C:
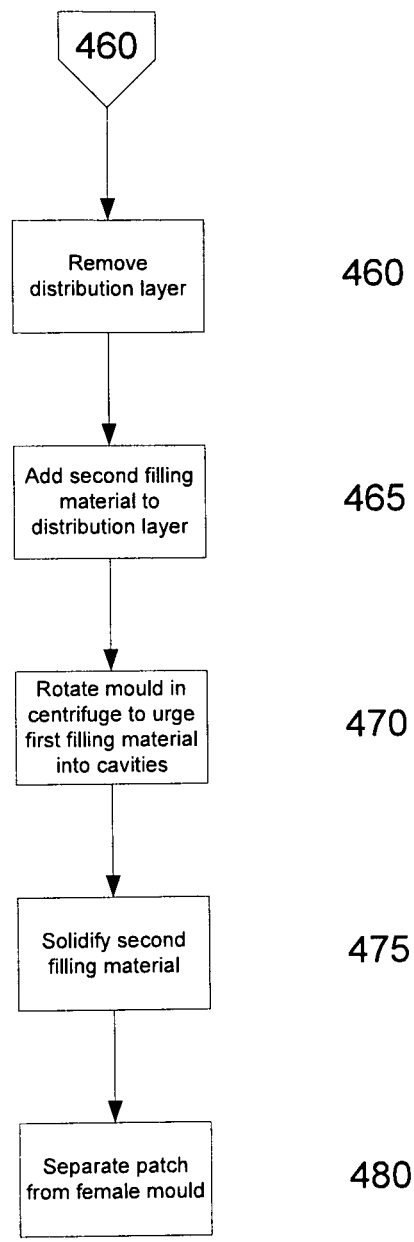

At step 240 the mold is removed from the solidified filling material as shown in FIG. 3D, with the solidified filling material forming a patch 100 having projections 110 and a base 120 thereby allowing the patch to be extracted from the mold and used.

By providing the distribution member, this ensures that filling material is distributed evenly over the mold surface 320, which in turn ensures even filling of the cavities. This can be useful in a number of situations.

For example, when producing patches having nano scale projections, such as a projection base diameter $d_3$ of <100 μm, the mold surface 320 will tend to be hydrophobic. Depending on filling material properties, this can cause the filling material to pool on the mold surface 310. As a result, when the fluid is urged into the cavities 310, cavities adjacent the pool of filling material will be filled preferentially to those separated from the pool. Whilst this issue could be addressed by providing an excess of filling material, this can be wasteful, resulting in more filling material being used than required. In the event that the filling material contains a biologically active material, such as a vaccine, or the like, this can lead to wastage, which is problematic when supply of the material is restricted for example due to limited availability, as can occur during mass vaccination programs, or the like.

Additionally, this technique can be used to allow a layered production process to be used. In this instance, multiple filling materials can be used to fill the cavities 310 in turn. Thus, for example, a first filling material may be used to fill the cavities to a first depth, with a second filling material being used to completely fill the cavities. In this instance, by distributing the filling material evenly over the mold surface 320, this ensures each cavity has an equal amount of first filling material, thereby ensuring even layering of the projections across the entire patch.

In the layering example, each filling material can contain a different payload, allowing the patch projections to deliver different payloads to different layers within the subject.

It will be appreciated that an excess of second filling material may be used to avoid the need for a second distribution member, although this is not essential. Layering can also be used to allow the patch base to be formed from a different material to the projections. This can be used for example to avoid the inclusion of payload in the base, which can in turn reduce waste.

Accordingly, the use of a distribution member can assist in allowing the formation of layered patches, as well as avoiding the use of unnecessary payload, such as biologically active materials.

By allowing the projections to be fabricated using a molding and casting approach, this can lead to a number of benefits.

For example, the projections can be formed from a wide range of materials thereby providing a greater flexibility in use. This can include fabricating the projections from materials that do not require the use of high temperatures during the casting process, allowing biologically active payloads to be incorporated therein, without being damaged by the casting process and without requiring prior encapsulation of the payload. This vastly simplifies the manufacturing process, allowing a wide range of payloads to be incorporated into the projections.

The projections can also be fabricated from a material such as a CMC, or the like that dissolves when brought into contact with a subject, thereby allowing embedded payloads to be successfully delivered to a subject.

During fabrication, a dispersion membrane can be used to evenly disperse filling material across the surface of the mold prior to casting, which in turn allows even filling of the mold to produce uniform projections across the patch.

Control of the amount of filling material used allows projections to be layered on a micrometer scale. Coupled with the ability of the projections to dissolve, this allows payload materials to be delivered to sites of interest within a subject, such as to specific layers or regions within the subject's skin. This can increase the efficacy of payload delivery, for example, by allowing vaccines to be delivered directly to immune cells in the skin, and therefore reduce the amount of payload material required to obtain a biological response.

The molding and casting approach can be performed using mold arrays, allowing a number of patches to be fabricated simultaneously. In on example, this can be achieved by using a molding plate and a casting plate, as will be described in more detail below. In one example, the molding plate can support the patch template during the molding process. After molding the plates are separated with the molds remaining in the casting plate. The dispersion membrane fits into the mold and the payloads are cast, before the arrays are dried in the molds situated in the casting template. The casting plate can be sealed and packaged for distribution, thereby reducing handling steps and facilitating a simple approach for scaling-up patch production. It will be appreciated that this allows large numbers of patches to be manufactured in a timely and cost effective manner.

A further example will now be described with reference to FIGS. 4A and 4B, and FIGS. 5A and 5B.

In this example, at step 400 desired patch properties are determined. The desired patch parameters will vary depending on the intended use of the patch and will include parameters such as the projection length, spacing, density, material or the like.

At step 405, a male mold is generated using the desired patch properties. The male mold may be formed in any one of a number of suitable manners depending on the preferred implementation. In one example, this is achieved through Deep Reactive Ion Etching (DRIE) of a silicon substrate.

Figure 5A:
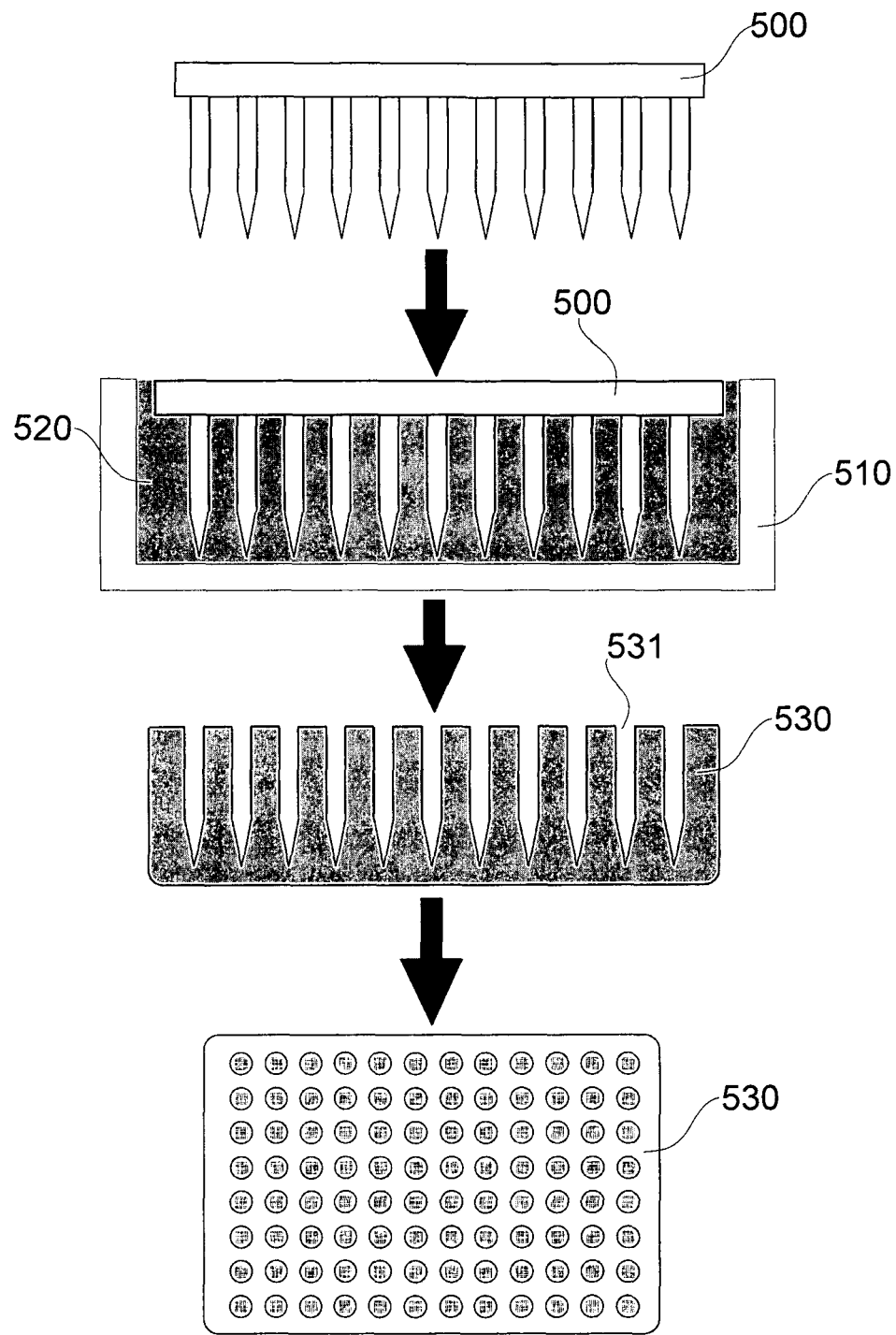
FIGS. 5A and 5B are schematic diagrams of the steps in the patch production process of FIGS. 4A to 4C.

Once the male mold has been produced, as shown for example at 500 in FIG. 5A, the male mold is immersed in a polymeric material, such as PDMS (Polydimethylsiloxane), at step 410. This may be achieved in any suitable manner but typically involves inserting the male mold 500 into a well 510 containing the polymer as shown generally at 520.

Whilst the male mold is immersed in the polymer the polymer may optionally be treated at step 415. The treatment can be used to ensure the polymer cures and sets and can include for example degassing the polymer to remove any unwanted gas, as well as baking the polymer to ensure it is sufficiently cured.

At step 420 the male mold is removed from the polymer to form the female mold 530, including cavities 531, as shown in FIG. 5A.

Once the female mold 530 has been formed, this can be used in creating patches. In this example, desired patch layers are determined at step 425. The desired patch layers may be determined in any one of a number of ways, but will typically depend on the intended use of the patch, and in particular where it is desired to deliver material to the subject.

Figure 6:
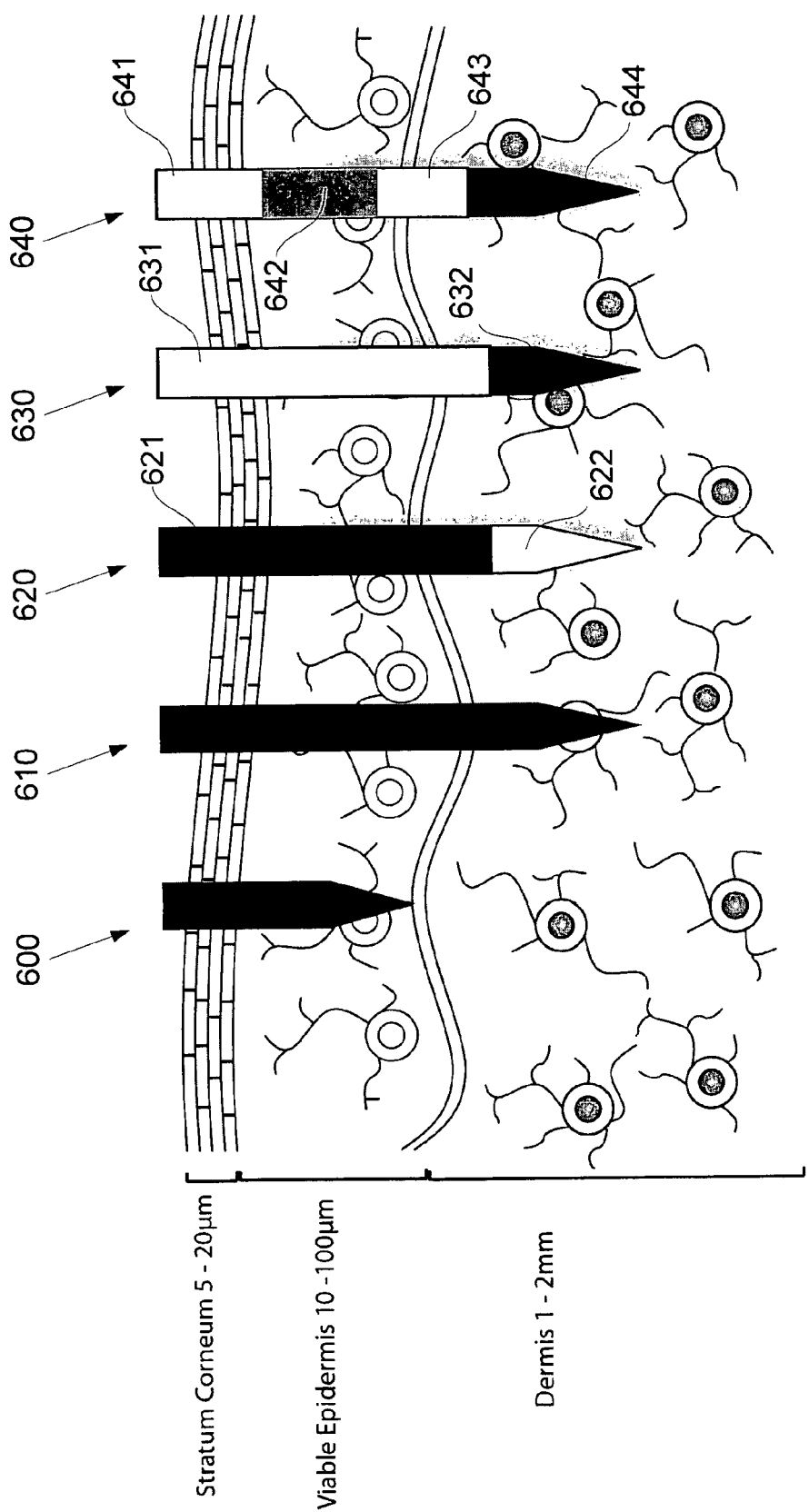
FIG. 6 is a schematic diagram showing the use of layered projections to deliver material to different regions in a subject.
Figure 7:
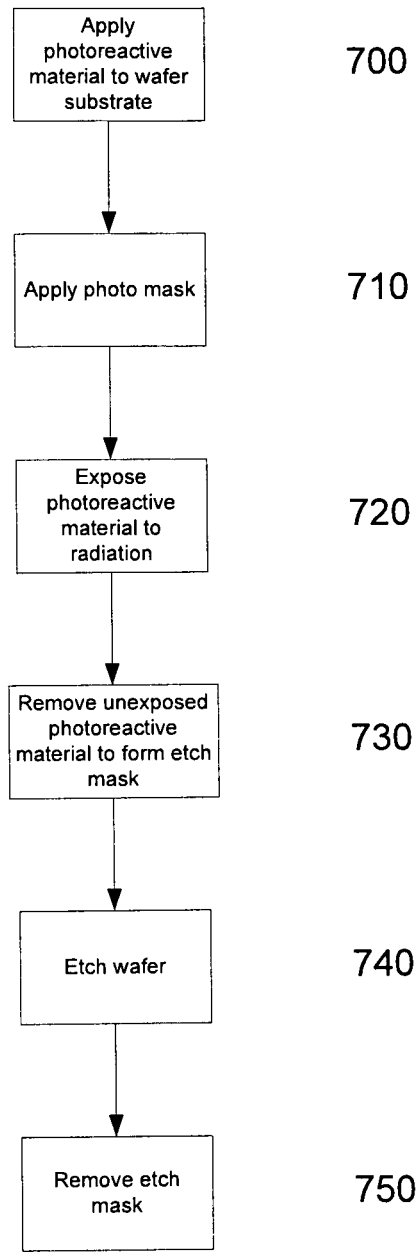
FIG. 7 is a flow chart of an example male mold production process.

In one example, each layer of the patch is adapted to deliver different payloads and/or stimulus to the subject, and/or to detect respective analytes in the subject. Accordingly, each patch layer can be formed using a different filling material. Additionally, each layer may have a desired depth to allow material in different layers to be delivered to different regions within the subject. An example of this is shown in FIG. 6.

In this example, a number of different projection configurations are represented by the projections 600, 610, 620, 630, 640. The projection 600 is made of a single filling material, defining a single layer, and has a length of approximately 100 µm so as to deliver material to the viable epidermis only. The projection 610 is also made of a single material, but has a length of greater than 100 µm so as to deliver material to both the viable epidermis and the dermis.

The projection 620 is made of two layers, each having a respective filling material. In this example, a first layer 610 is approximately 100 µm in length so as to deliver first material to the viable epidermis, while the second layer 622 is positioned at the end of the first layer so as to deliver material to the dermis only. The projection 630 is similarly made of two layers, with the first and second filling materials reversed.

The projection 640 is made of four layers 641, 642, 643, 644 each having a respective filling material. In this example, a first and second layers 641, 642 are positioned in the viable epidermis, the third layer 643 bridges the viable epidermis and dermis, delivering material to both regions, whilst the fourth layer 644 is provided in the dermis.

Following determination of the patch layers to be used, filling solutions are selected at step 425. During this process, the filling solutions may be selected to have certain properties to help ensure even filling of the cavities. This can take into account mold properties, such as the cavity size, cavity shape, cavity spacing, cavity surface properties and mold materials, which in turn can have an impact on the ability of the filling material to enter the cavity. Accordingly, it is typical to select solution properties, such as the surface tension and viscosity, to ensure even filling of the cavities.

The surface tension can be between 0.023 N/m and 0.073 N/m, but is not limited to these values. Viscosity can be $10^{-3}$ Pa·S and 10 Pa·S, but can be much higher if need be. The above described methodology does not depend particularly on specific surface tensions/viscosities so the ranges for these solutions can be broad.

The filling material properties can be controlled through the addition of one or more other agents such as a viscosity enhancer, a surfactant, or a detergent, and an adjuvant. These ingredients can be provided in a range of different concentrations. For example, the viscosity enhancer or surfactant can form between 0% and 90% of the filling material.

A range of different viscosity enhancers can be used and examples include methylcellulose, CMC, gelatin, agar, and agarose and any other viscosity agents. The filling material typically has a viscosity of between $10^{-3}$ Pa·S and $10^{-1}$ Pa·S. In one example, using a filling material containing 1-2% methylcellulose, which results in suitable uniform filling, resulting in a viscosity within the range $010^{-3}$ Pa·S and 10 Pa·S.

Similarly, a range of different surfactants can be used to modify the surface tension of the filling material, such as any suitable agent that changes surface tension, and that is biocompatible at a low concentration. The filling material properties are also typically controlled through the addition of one or more other agents such as a viscosity enhancer, a detergent or other surfactant, and an adjuvant. These ingredients can be provided in a range of different concentrations. For example, the viscosity enhancer or surfactant can form between 0% and 90% of the filling material.

Additionally, one or more payloads or other materials may be selected for inclusion in the filling material. Examples of suitable materials include:
- nanoparticles;
- a nucleic acid or protein;
- an antigen, allergen, or adjuvant;
- parasites, bacteria, viruses, or virus-like particles;
- quantum dots, SERS tags, raman tags or other nanobiosensors;
- metals or metallic compounds;
- molecules, elements or compounds;
- DNA;
- protein;
- RNA, siRNA, sfRNA, iRNA;
- synthetic biological materials;
- polymers; and,
- drugs.

Following determination of the filling material, filling material volumes required to create the respective layers are calculated at step 435. The volumes are calculated based on the required depth of the layer and the geometry of the cavity, which is in turn known from the dimensions of the projections on the original male mold 500. A number of other variables may also be taken into account when determining the volume delivered into the mold shaft, including the filling material viscosity and concentration, diameter of the hole at the PES mold junction, centrifugation force, pore size of the filter, filter material, and filter loading volume.

At step 440, a permeable distribution member 540 can be provided on top of the female mold 530. In one example, the permeable member is formed from any material which allows the filling material to diffuse therethrough, such as PES. PES provides a fast flow rate, uniform 3-dimensional architecture and low protein binding. Furthermore, various pore sizes are available, although a pore size of 220 nm was utilized to cast protein solutions into the molds.

At step 445 the required volume of first filling material 550 is added to the distribution member 540. The filling material can be added in any suitable way but in one example this is achieved using a dropper 552, such as a pipette, to allow the filling material to be applied to the distribution layer one or more droplets. It will be appreciated however that any suitable technique that allows the volume of fluid to be controlled may be used. Once the added the filling material diffuses throughout the distribution member 540, as shown at 541, thereby ensuring that filling material is provided above each cavity 531.

Figure 5B:
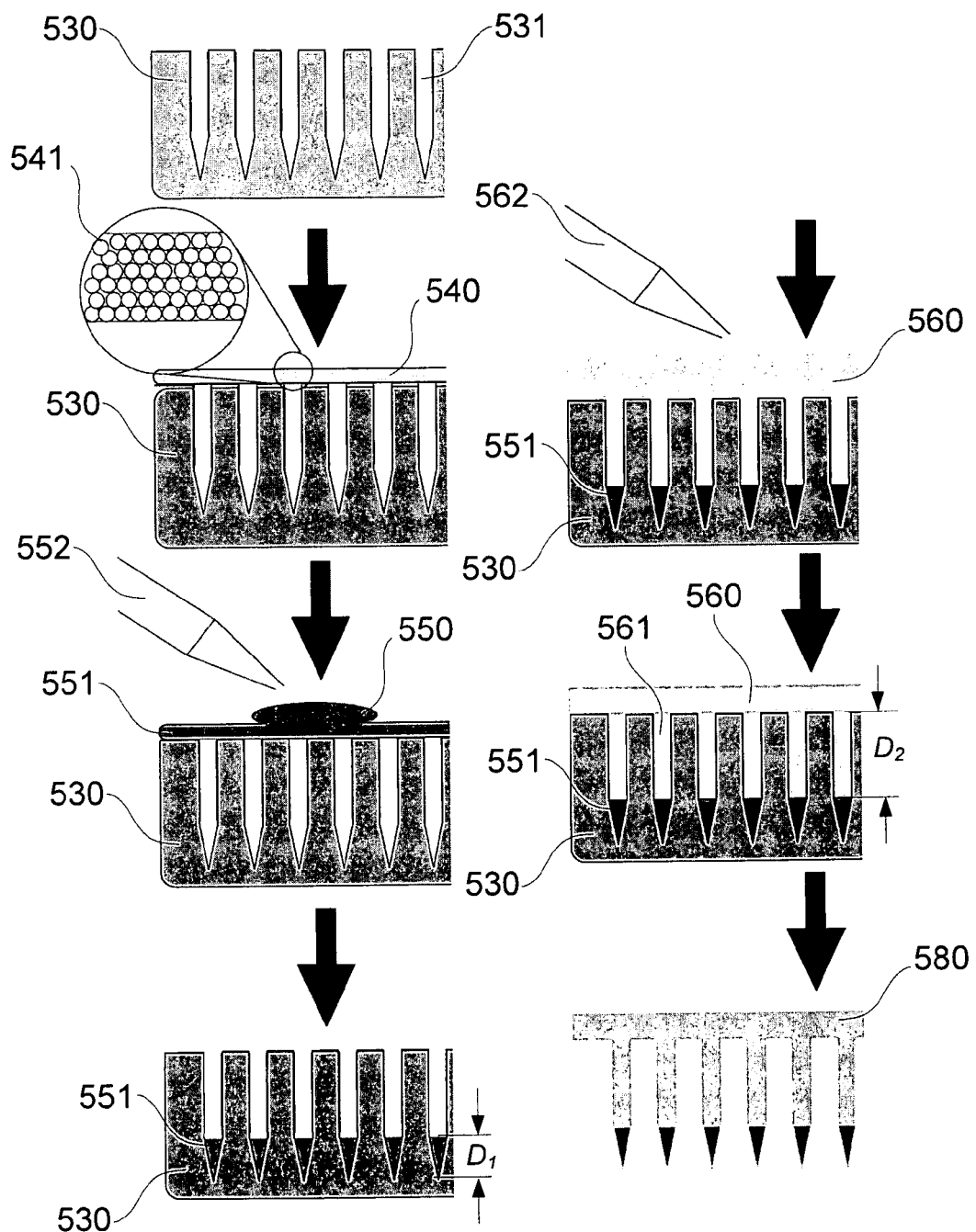

At step 450, the mold is rotated in a centrifuge to urge the first filling material into the cavities 531. As shown in FIG. 5B, the first filling material 542 fills the cavities to a depth $D_1$ controlled based on the volume of filling material 550 added to the distribution layer 540 at step 435.

At step 455 the first filling material is solidified and this may be achieved in any suitable manner such as through baking, exposure to ambient conditions or radiation, or the like. This step may not be required, for example, if the viscosities and/or surface tensions of the filling materials are such that the filling materials will not mix.

It will be appreciated that the above steps can be performed simultaneously by performing the centrifugation under suitable conditions, such as at a specific temperature or for a specific duration.

At step 460 the distribution layer is removed before the second filling material 560 is added using a dropper 562 at step 465. In this instance a distribution layer is not required as excess second filling material is used to form the patch base.

At step 470, the mold is again rotated in a centrifuge to urge the second filling material 561 into the cavities 531, as shown at 561, whilst second filling material 560 remains on the mold surface. Following this the second material is solidified at step 475 allowing the created patch 580 to be separated from the female mold at step 480.

In this regard, the second filling material can be solidified whilst the second permeable distribution layer is in place so that the second permeable distribution layer also forms part of the patch substrate. However, this is not essential and the permeable layer may be removed with the upper surface of the mold simply being filled with second filling material, to form the substrate. During casting of the second layer, the first layer may be hydrated facilitating fusion between the first and second layers. This fusion can assist in forming solid projections during the drying process resulting in a single solid structure on removal from the mold.

An example of the process for creating a male mold will now be described with reference to FIGS. 7 and 8A to 8C.

In this example, at step 700, a photoreactive material, such as Su-8, which is a photoreactive polymer, is applied to a substrate 800, which in one example is 4 inch, 800 μm thick 100 silicon wafer. The substrate 800 is then spun at an appropriate speed to distribute polymer in a layer 810 over a surface 801 of the substrate 800. The spin speed is selected to control the thickness of the mask layer 810. In one example, to form a projection having a length in the region of 80-70 μm, the mask layer 810 has a thickness in the region of 7-8 μm. It will be appreciated that a thicker mask, such as up to 20 μm may be used.

The substrate 800 and mask layer 810 are optionally treated. This may be performed, for example to remove any excess solvent, which can be achieved by soft baking the substrate 800 and layer 810 for five minutes at 95° C.

Once suitably prepared, the mask layer 810 can be selectively exposed with radiation 820 to cause the exposed mask material to harden. In one example, this is achieved by applying a suitable photo-mask 830 at step 710, before exposing the photo mask and ask layer 810 to radiation from a radiation source at step 720. Thus, exposure of the Su-8 film can be performed using chromium on quartz photo-mask and a Carl Suss MA6 mask aligner set to supply 10 ml/second UV light. Typically complete cross-linking of the Su-8 polymer occurs after 1.8 seconds of exposure for 1 μm of Su-8 thickness, although longer exposure of up to 30 seconds can be used to ensure complete cross-linking.

The substrate 800 and mask layer 810 may again be optionally treated, for example by baking for one minute at 95° C. This can be used to promote the formation and release of a Lewis Acids which aids the cross-linking process and formation of a straight sidewall profile for the mask.

The unexposed mask material can be removed using a suitable solvent at step 730. Thus, in the above, the uncross-linked Su-8 can be removed by developing in EC solvent (PGMEA) for two minutes. The complete removal of uncross-linked Su-8 can be confirmed by washing the wafer with IPA. If a white precipitated is observed (indicating uncompleted development) the wafer is replaced in the EC solvent for further 30 seconds. Development is completed until no white precipitated is observed upon washing with IPA. The excess IPA can be removed by blow drying with dry nitrogen gas.

Figure 8A:
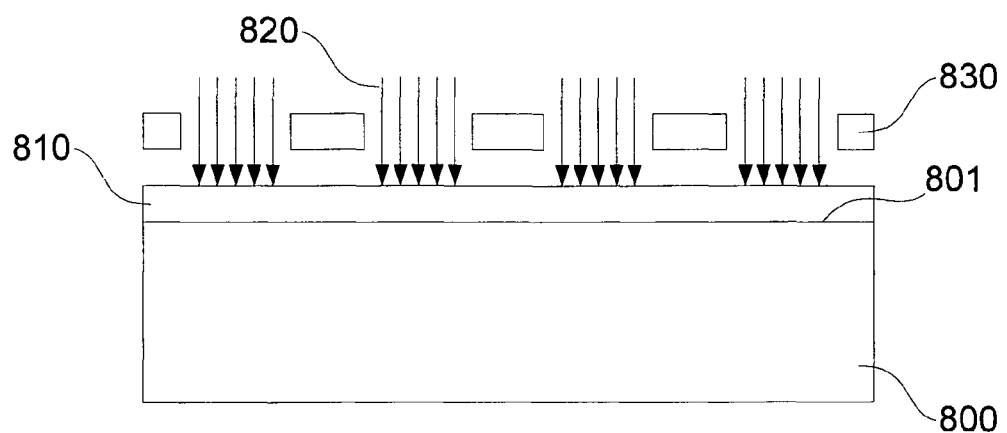
FIGS. 8A to 8C are schematic diagrams of the steps in the male mold production process of FIG. 7.
Figure 8B:
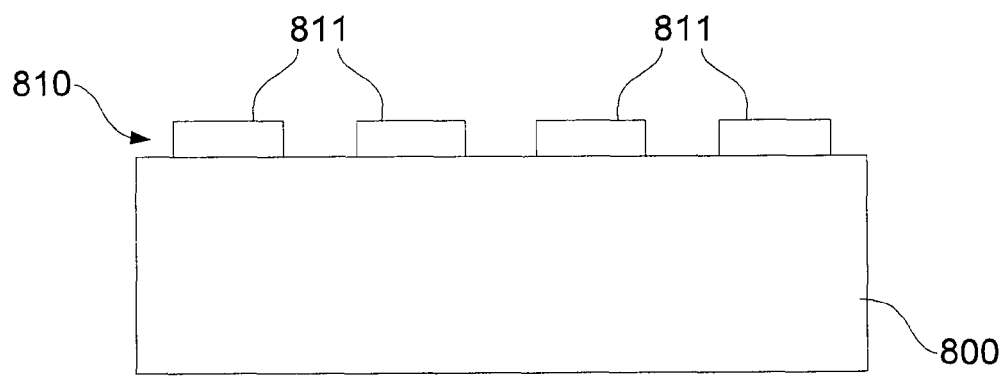

Further treatment may then be performed, such as hard baking of the wafer 800 at 100° C. for five minutes. This can be used to harden and remove residual developer and IPA for the Su-8 mask. At this stage in the process, the mask layer 810 includes a number of dots 811, as shown in FIG. 8B.

The next stage in the process is the formation of projections by etching at step 740. In one example, this is achieved using plasma etching, which can be completed on an STS (Surface Technology Systems) ASE (Advanced Silicon Etch) system. In one example, this is achieved using $SF_6$ as the etch gas and $C_4F_8$ as the passivation gas, although as described above, other gases can be used.

Controlled continuous isotropic plasma etch process was complete with a plasma gas mixture of $SF_6:C_4F_8$ typically in the ratio range of 0.25 to 0.60. Vertical, horizontal and needle tip angle can be controlled to provide require needle profile. This is achieved by ramping or varying the plasma gas condition throughout the etch process, by changing the rate of gas flow, pressure and $SF_6:C_4F_8$ ratios.

Figure 8C:
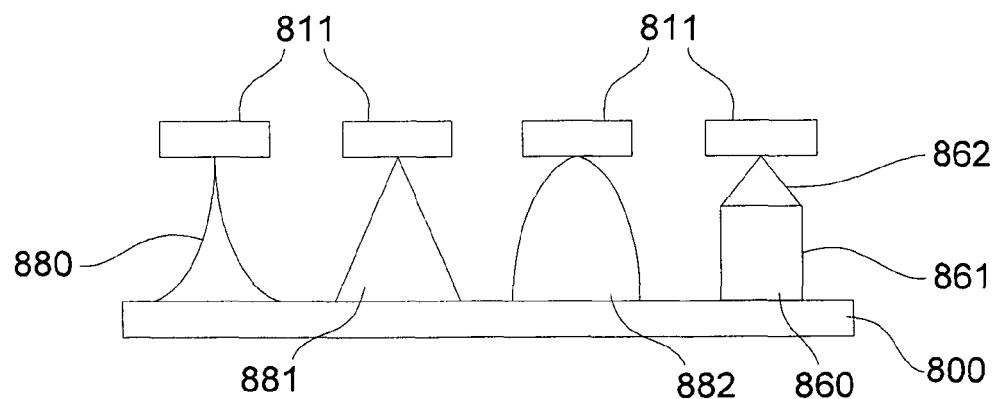

In one example, by performing a continuous etch for approximately 30-60 minutes, needle profiles of concave to convex shapes can be achieved, as shown at 850, 851, 852 in FIG. 8C.

A further alternative, etching can be performed in multiple stages to provide additional control. In one example, a continuous etch is performed for approximately 30-60 minutes, with a subsequent etch being performed for a further 15-30 minutes. This allows a projection 560 having a column shaped supporting section 561 and a conical tip 562 to be produced, as shown in FIG. 5C.

In one example, the profile of the projection can be formed by altering etching parameters, such as the $SF_6:C_4F_8$ ratio, pressures, or the like, between the different etch steps.

Additionally, the wafer 800 can be removed from the ASE system, allowing the wafer and/or passivant to react with the ambient atmosphere. This can alter the effect of the passivant, thereby altering the profiles that can be produced.

The ability to pause the etching process allows further control over the etching process. For example, the etching can be performed to near completion, with the process then being halted to allow the wafer or patches to be examined to determine the amount of etching required to complete the process. The process can then be resumed and completed.

Once completed the remaining etch mask is removed at step 750. This process is described in further detail in copending patent application number WO2009/09766.

A number of example experiments will now be described. For the purpose of these experiments, patches were constructed using the following protocol.

Male mold construction: In this example, the male mold is in the form of patch having a number of projections provided on a surface of a substrate. The projections and substrate may be formed from any suitable material, but in one example, are formed from a silicon type material, allowing the device to be produced using processes such as vapour deposition, silicon etching, Deep Reactive Ion Etching (DRIE), or the like. The projections are therefore typically solid, non-porous and non-hollow, although this is not essential. Alternatively arrays or single projections can be made using micro machining and/or etching techniques.

An example male mold is shown in FIGS. 9A and 9C. In this example, the male mold is a 5 mm×5 mm array of gold-coated silicon projections. The array includes 3364 projections uniformly spaced in a square grid formation 70 μm apart. Each projection includes a cylinder shaft approximately 61 μm±3 μm in length topped with a cone of approximately 51 μm±2 μm length. The total length of the projections was 112 μm±4 μm with a base diameter of 35 μm±2 μm. The stepped configuration of the projections can be produced using a two stage etching process, as described above and in copending patent application number WO2009/097660. However, this is not essential and any projection and/or patch geometry can be used.

Female mold construction: Polydimethylsiloxane is used extensively in the area of microfluidics, micromolding and microfabrication in both biological and non-biological applications. Its ability in accurately molding microstructures and curing to form a non-adhesive inert solid makes it especially useful as molds for the fabrication of projections. Female micromolds were constructed out of PDMS using a 58×58 array of gold-coated silicon projections (height~130 μm, diameter~30 μm). An example of the female mold constructed using the patch of FIGS. 9A and 9C is shown in FIGS. 9B and 9D. Comparison using SEM analysis shows that PDMS molding accurately and reproducibly creates female micromolds of the projection array.

The male mold is washed (i.e. 70% ethanol) and dried at ambient conditions and stored in a petri-dish with projections facing upwards. The PDMS is mixed with curing agent. The polymer mixture is then poured over the male mold so as to immerse the male mold to a depth of approximately 5 mm. The immersed male mold can then be placed under vacuum for about two hours or until no gas bubbles are visible. Following degassing the combined mold is placed in an oven at 65° C. overnight to cure. After the PDMS had cured, the female master molds are removed and cut to fit a standard biological 96-well plate. In preparation for casting, the molds can be thoroughly washed in water followed by 70% ethanol and dried at 50° C.

In one example, during construction of the female mold, the male mold can be attached to a support, an example of which is shown in FIGS. 10A to 10E. In this example, the support 1000 includes a substantially circular base 1001, and a plinth 1002, having tapered edges 1003 and a flat surface 1004 for receiving the male mold 1005. The tapered edges 1003 are arranged so that when the female mold 1010 is created, the female mold includes a 'trough' shape 1011 for receiving payloads during the casting process. An example of the resulting patch is shown in FIG. 10E.

Figure 11A:
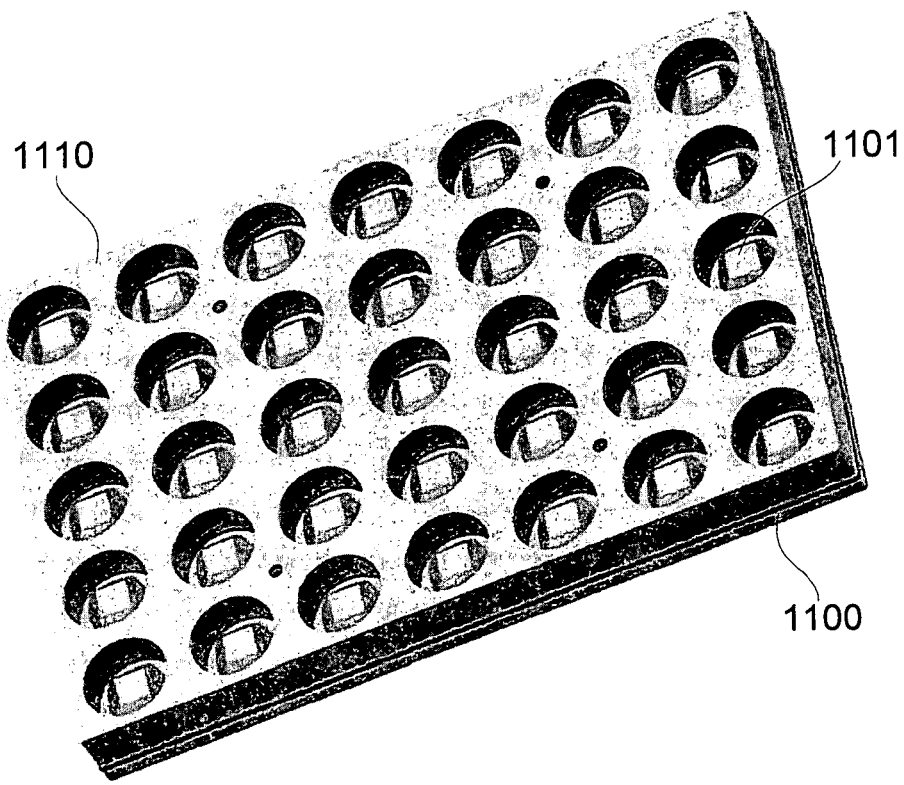
FIGS. 11A and 11B are schematic diagrams of an example of a molding plate and casting plate.
Figure 11B:
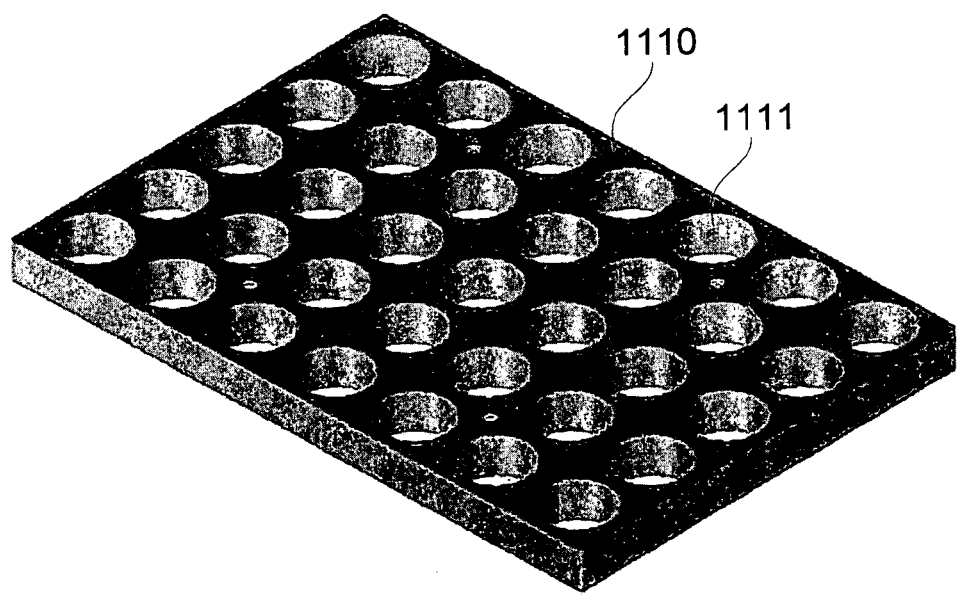
Figure 11D:
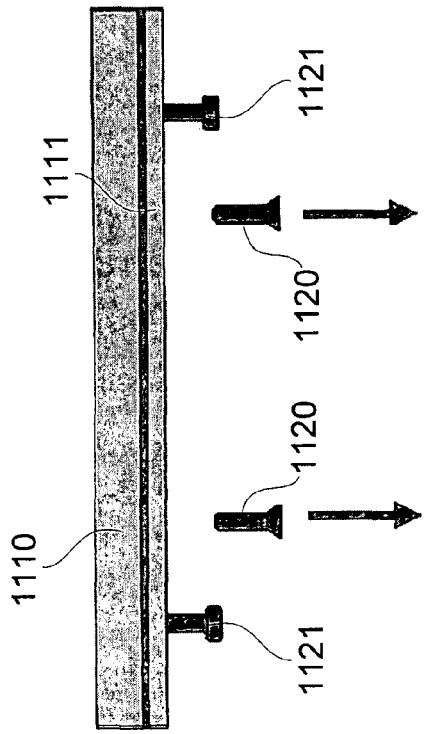
FIGS. 11C to 11F are schematic diagrams of an example of a molding plate and casting plate.
Figure 11F:
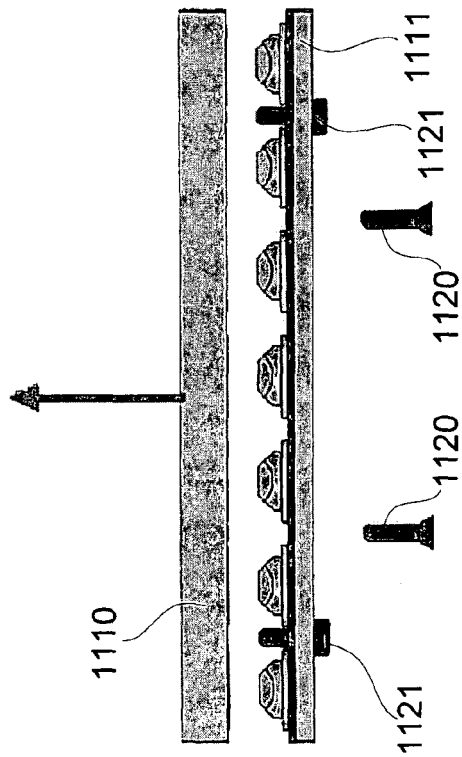
Figure 11C:
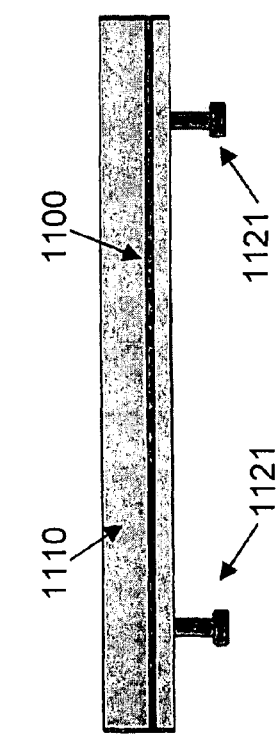
Figure 11E:
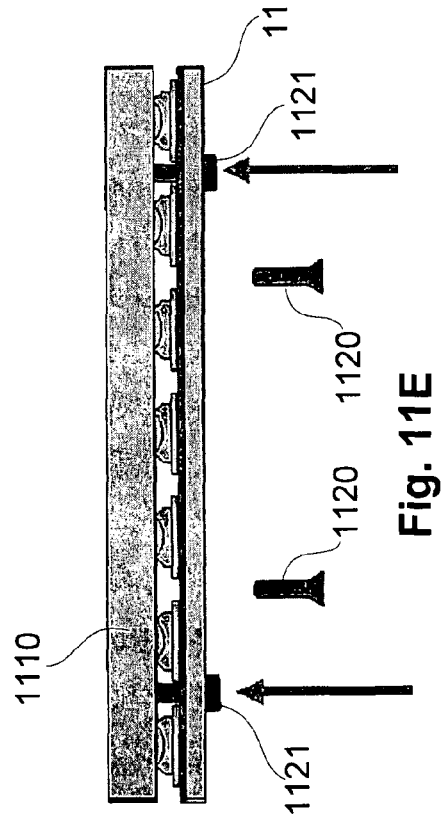

To allow a number of patches to be created in a single casting process, female molds can be created in an array using a molding plate and casting plate, examples of which are shown in FIGS. 11A and 11B. In this example, the molding plate 1100 includes an array of supports 1101, similar in arrangement to the supports 1000 shown in FIG. 10A. The casting plate 1110 includes a number of apertures 1111, which align with the supports 1101 when the molding and casting plates are coupled together, which in one example is achieved using locking screws 1120.

In use, mold material is provided into the apertures 1111, and allowed to set. As shown in FIGS. 11C to 11F, once the mold material has set, the locking screws 1120 are removed, before release screws 1121 are screwed into the molding plate 1100, thereby urging the casting plate 1110 away from the molding plate 1100. The removed casting plate 1110 can then be used to cast a number of patches in a single casting process. To achieve this, a single dispersion member can be provided on the casting plate, so that the dispersion member can be used to supply filling material to each of the female molds contained in the array. Once the filling material has been provided, the array is dried with the molds in situ. The entire casting plate can then be sealed and packaged for distribution. This reduces the number of handling steps required to prepare the patches.

Example casting processes to produce a variety of patches will now be described.

Single-layer casting: The PDMS molds can be used to produce dissolving projections and due to its durability and non-adhesive properties, the molds can be reused to make multiple projections. Carboxymethylcellulose, an FDA approved cellulose derivative, was used in production of the projections, thereby allowing the projections to dissolve once in contact with a subject. The viscosity of casting solution contributed directly to the time taken to dry the projections and the amount applied for casting.

Figures 12A, 12B, 12C:
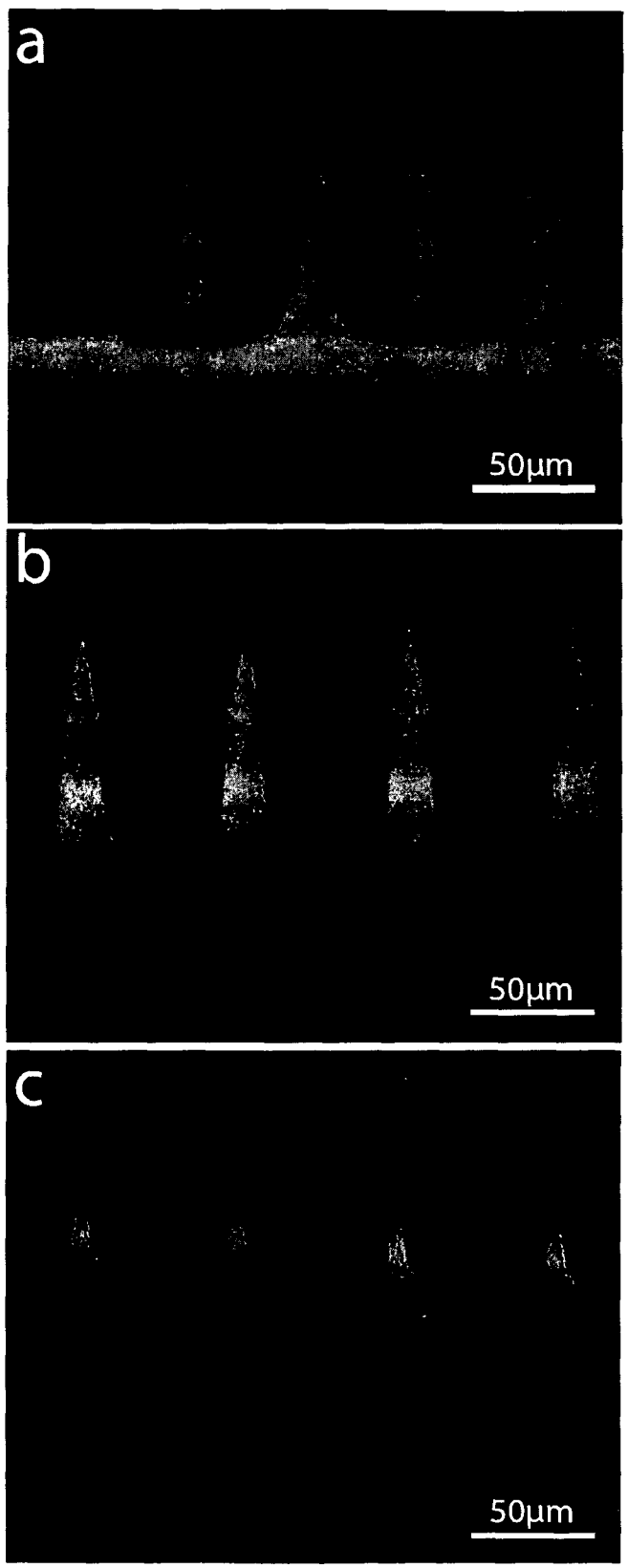
FIGS. 12A to 12C are fluorescence images of projections including different layer configurations.

Rhodamine-dextran projections were produced by mixing 1 μL of 2.5 mM rhodamine-dextran (40,000 MW, Sigma-Aldrich) with 9 μL of 0.22 mM carboxymethylcellulose (CMC, 90,000 MW, Sigma-Aldrich) solution, which was added to the surface of the female molds. The molds were then centrifuged at 3000 g for 2 hours to facilitate compaction and drying. The molds were then placed in a sealed desiccator at 22° C., until solution had dried. The dissolving projection array was then removed from the molds and stored in a sealed desiccator at 22° C. To assess the morphology of the projections produced, fluorescent microscopy was then used to validate the projections. An example florescence image of a single layer projection is shown in FIG. 12A.

In this example, the dissolving projections formed, are solid with a uniform dispersion of both the CMC and rhodamine-dextran. The projections accurately represented the male microstructure however; there was a reduction in size of the projections in relation to the male microstructure of approximately 28% in all dimensions. This reduction in size produced projections of 94 μm±2.8 μm in length and 23 μm±1.1 μm base diameter with extremely sharp tips (radius of curvature typically <1 μm, often <100 nm).

Dual-layered array construction: Polyethersulfone (PES), a porous material (thickness ~220 μm and porosity 0.22 μm), known as a "membrane". The membrane was cut to fit the surface of the molds in the multiwell plate. The multiwell plate allows for one individual to make many (10 s to 100 s) of dissolvable arrays at a time. A volume (i.e. 5-10 μL) of solution containing active compound and/or sugar-based excipient (usually carboxy-methylcellulose, CMC) is pipetted onto the surface of PES. Molds with loaded PES in place are then centrifuged at 3000 g for 1-30 minutes. The PES can then be removed and any excess solution removed with empty PES. Molds are then centrifuged again at 3000 g for 10 minutes to allow further compaction and drying. A viscous solution containing 1-15% CMC can then be added to molds providing the array backing layer. The molds are then centrifuged at 3000 g for 20 minutes. The molds are then placed in a sealed desiccator at 4-22 C, until solution has dried. The dissolving projection array can then be removed from molds and stored in a sealed desiccator between −80 C to 22 C. An example florescence image of a dual layer projection is shown in FIG. 12B.

Multi-layered array construction: Polyethersulfone is cut to fit on the surface of the female molds in a multiwell plate. A volume (i.e. 5-10 μL) of solution containing active and/or sugar-based excipient can be pipetted onto the surface of PES. Molds are then centrifuged at 3000 g for 1-30 minutes. The PES dispersion membrane and excess solution removed. Molds are then centrifuged again at 3000 g for 1-30 minutes to allow for further compaction and drying. For additional layers, fresh PES can be placed on the surface of the mold and a volume (i.e. 5-10 μL) of solution containing second active and/or sugar-based excipient can be pipetted onto the surface of the PES. Molds are then centrifuged again at 3000 g for 1-30 minutes to allow for further compaction and drying.

For additional layers, fresh PES was placed on the surface of the mold and 5 μL of solution containing 1 μM FITC-dextran (2,000,000 MW, Sigma-Aldrich) or 0.23 mM Evans Blue (85% dye, Sigma-Aldrich) mixed with 0.22 mM CMC was pipetted onto the surface of the PES. Molds were then centrifuged at 3000 g for 5 minutes to allow for further compaction and drying. This process can be repeated to achieve the desired yield of multiple layers, and thickness of layers, containing different payloads and/or excipients.

Finally a backing layer was applied using 2.1 mM CMC. The molds were then centrifuged at 3000 g for 20 minutes. The molds were then placed in a sealed desiccator at 22° C., until solution had dried. The dissolving projection array was then removed from molds and stored in a sealed desiccator at 22° C. An example florescence image of a multi-layer projection is shown in FIG. 12C.

In one example, Rhodamine-dextran was mixed with CMC solution and added to the surface of a polyethersulfone (PES) membrane. The porous membrane absorbed and evenly dispersed the fluorescent solution across the surface of the female mold followed by casting. A second reagent was cast into the mold to produce fluorescent multilayered dissolving projections. To limit active payload to the projection shafts, a backing layer of CMC with no active compound was cast into the female mold. Production of the micro-layered dissolving projections produced solid projections with even dispersion of the active compound within the array.

Figure 13A:
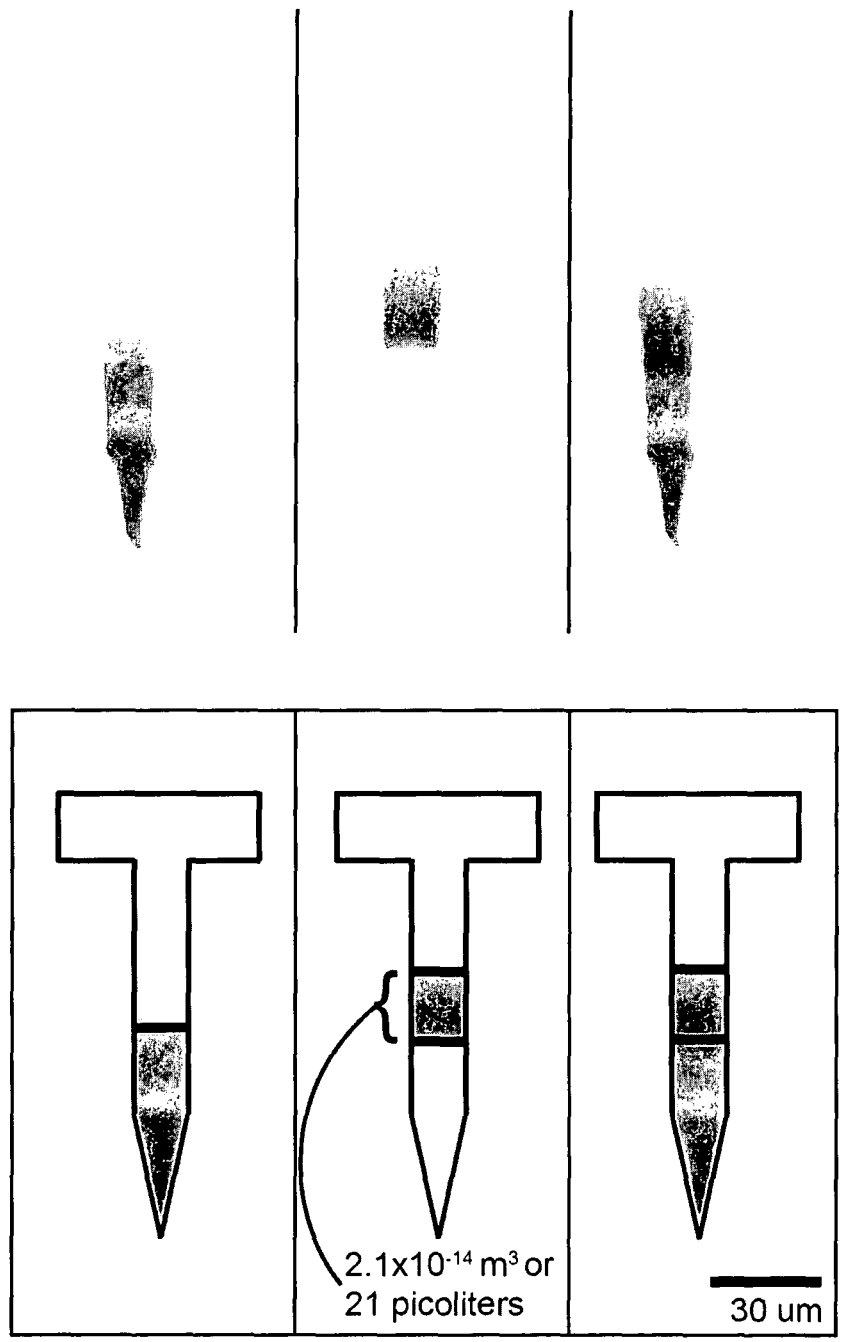
FIG. 13A is a fluorescence image of examples of multi-layered projections showing layer volumes.
Figure 13B:
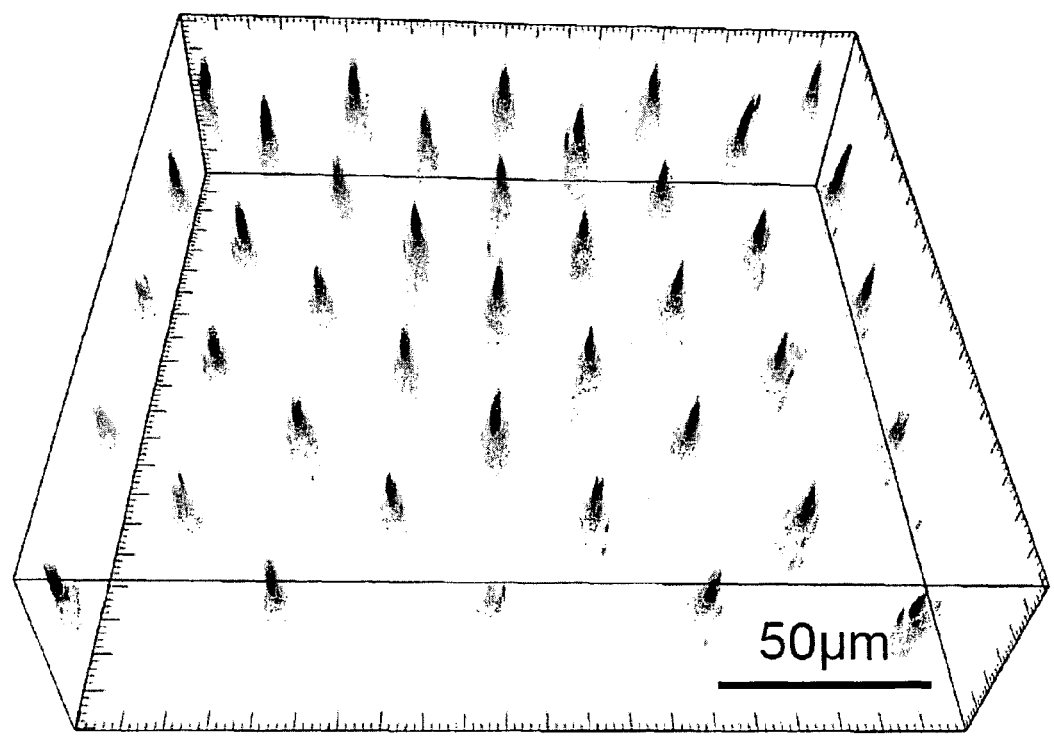
FIG. 13B is a fluorescence image of an example of a patch with 70 μm fluorescent silica particles concentrated in the projection tips.

The production method is able to produce micron-sized layers with picoliter volumes, as shown in FIG. 13A. FIG. 13B is a fluorescent confocal image showing a patch with 70 μm fluorescent silica particles concentrated in the tips. The patch contains a backing layer of carboxymethylcellulose with no fluorescent payload and was excited with 550 nm wavelength. This further highlights the ability to concentrate payload in a specific region of the projections.

Figure 14:
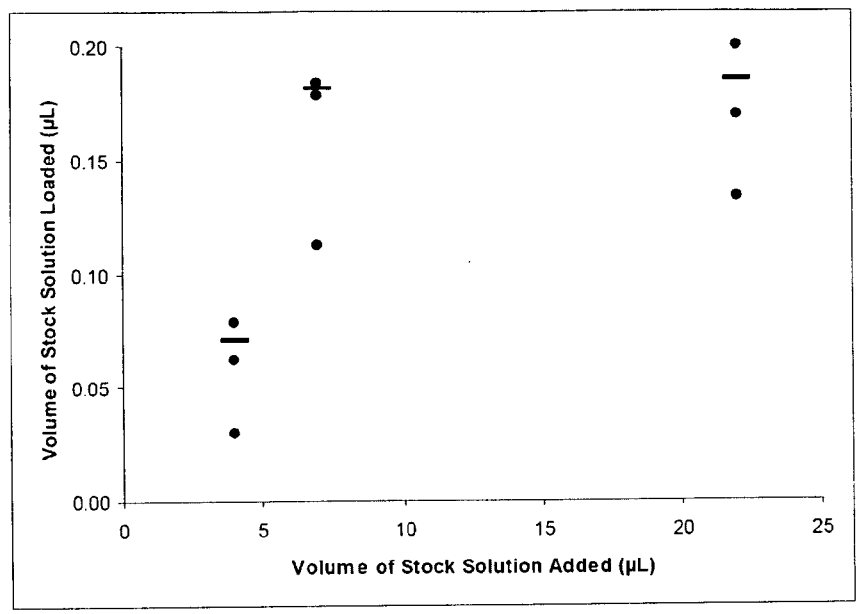
FIG. 14 is a graph showing relative volumes of supplied and fluid loaded when loading the female mold.

The volume of the example female mold is calculated to be 0.22 μL. Varying the amount of solution cast into the mold using the above casting method results in approximately 80% of the female mold layered, as shown in FIG. 14.

The penetration characteristics of projections entering skin are dictated both by the surface of the skin and the rigidity of the projection material. Skin elastic properties include those of the stratum corneum, viable epidermis and dermis, which have a Young's modulus of 26-120 MPa (depending on hydration), 2.9-11.1 MPa and 2.1-4.3 MPa, as described in Y. Yuan, R. Verma, Colloids and Surfaces B: Biointerfaces 2006, 48, 6, M. A. Kendall, Y. F. Chong, A. Cock, Biomaterials 2007, 28, 4968 and F. H. Silver, G. P. Seehra, J. W. Freeman, D. DeVore, Journal of Applied Polymer Science 2002, 86, 1978, respectively. The Young's elastic modulus of the projections based on the excipient (CMC) is 1 GPa. On a scale similar to the projections, the skin surface fails, facilitating penetration at ~13 MPa.

For the 'fixed-pinned' case where the base of the projection is fixed in position and the tip can move freely, assuming the projection is a cylinder 100 μm in length with a radius of 10 μm, buckling load of CMC projections can be calculated using Euler's buckling equation (1):

$$F_{buckling} = \frac{\pi^2 EI}{(kL)^2} \quad (1)$$

$$F_{buckling} = P_{buckling} \times A_{projection\_tip} \quad (2)$$

where:
- $F_{buckling}$ is the force to buckle the projection;
- $P_{buckling}$ is the pressure at buckling;
- $A_{projection\_tip}$ is area of the projection tip being loaded during penetration;
- E is the elastic modulus of CMC;
- I is the area moment of inertia of the projection;
- k is the length factor for the 'fixed-pinned' case; and
- L is the length of the projection.

Using the above information the pressure required to buckle an individual cylinder projection comprised of CMC is 50.4 MPa. This is greater than the pressure of failure for the skin of ~13 MPa reported, therefore, predicting that the projections can successfully penetrate the skin.

A number of in-vivo experiments to test the ability of the projections to penetrate the skin and deliver material to a subject were performed as outlined below.

Multi-Photon Microscopy

PES filter paper was cut to fit the surface of the molds in the multiwell plate. Vaccine formulation containing 0.8 mg/mL Quil-A (Brenntag Biosector) and 0.67 mM ovalbumin (Sigma-Aldrich) in MilliQ water was prepared and 10 µL was pipetted onto the surface of PES. Molds with loaded PES in place were then centrifuged at 3000 g for 10 minutes. The PES was then removed with any excess formulation. Molds were then centrifuged at 3000 g for 10 minutes to allow further compaction and drying. A viscous solution containing 1.4 mM CMC was then added to the molds to provide the array backing layer. The molds were then centrifuged at 3000 g for 20 minutes. The molds were then placed in a sealed desiccator at 22° C., until the formulation had dried. The dissolving projection array was then removed from molds and stored in a sealed desiccator at 22° C. until vaccination. Low dose dissolving projections were also prepared using the above procedure, however with 33.8 µM ovalbumin.

Female C57 black mice were anesthetized with an intraperitoneal injection of 150 µL of 10 mg/mL ketamine and 2 mg/mL xylazil in sodium chloride. The mice were then administered 200 µL of 10 mg/mL Hoechst 33342 intravenously. A rhodamine-dextran projection array with carboxymethylcellulose backing was applied to the ventral side of the ear. Application was with a spring applicator at 1.9 ms$^{-1}$ for 5 minutes. Following administration the projections were removed and the administered area was examined using confocal microscopy. The wavelengths used to excite the rhodamine-dextran and Hoechst 33342 was 543 nm and 770 nm respectively.

Figure 15:
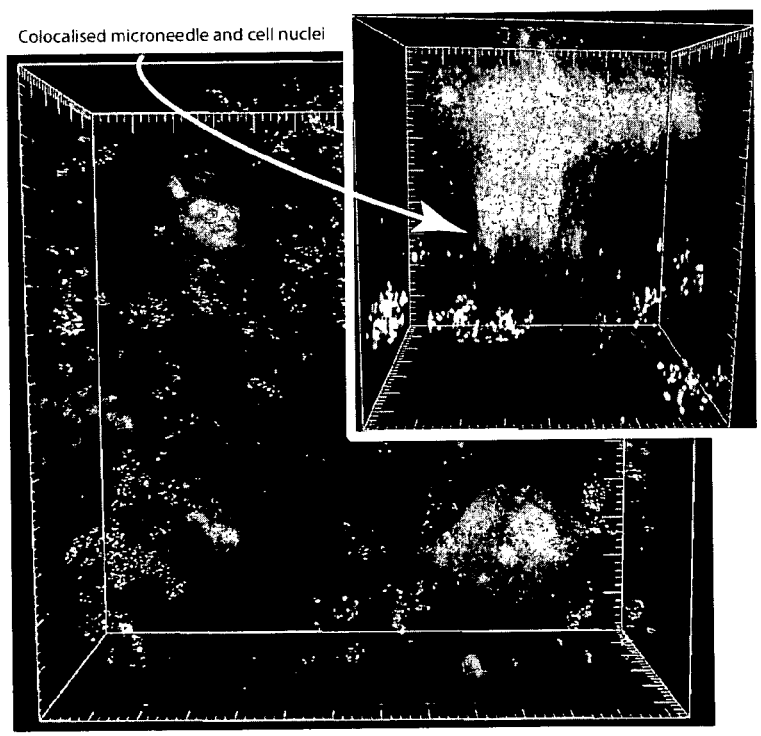
FIG. 15 is a fluorescence image showing colocalisation of a projection and cell nucleus.

It was found that the projections reliably penetrated the skin of the mouse ear, with dissolution of the projections within five minutes. The projections penetrated to a depth of approximately 30-50 µm. This is an ideal depth for viable epidermal delivery and is verified by the colocalisation of projection and cell nucleus as can be seen in FIG. 15.

Cryo-SEM

Figure 16:
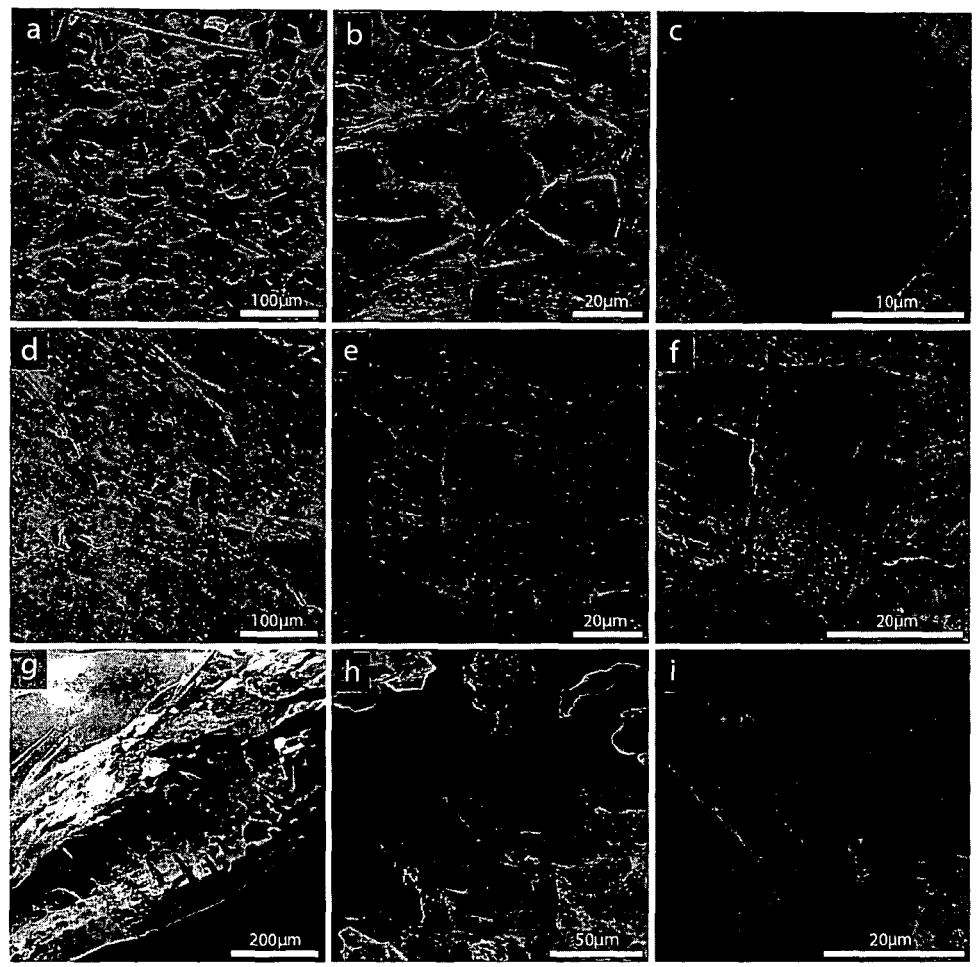
FIGS. 16A to 16i shows SEM photographs showing penetration of a dissolving projection.

Dissolving projections composed of carboxymethylcellulose were applied to the skin at 1.9 ms$^{-1}$ using a spring applicator. The ear and projections were then snap-frozen in liquid nitrogen following removal of the projections. The time taken between application and snap-freezing was less than a minute. SEM analysis of the ear shown in FIGS. 16A to 16C shows that the projections reliably penetrated the skin. On removal, a large majority of the projections remained in the skin, as shown in FIGS. 16D to 16F.

SEM photograph shown in FIGS. 16G to 16I, show partial penetration of a dissolving projection. It can be seen that the base of the projection has already begun to dissolve and has fused to the surface of the skin. The projections have dissolved and anchored in the skin preventing removal. To show the dissolution process projections were applied for approximately two minutes and slightly removed before snap-freezing. A large majority of the projection shafts have completely dissolved in the skin, which can be seen in the Figures.

Optimal cell targeting is required to achieve maximum response from an administered payload. The ability to control and layer the payload within specific areas of the projection especially the tips, allows for greater chances of payload delivery. Rapid dissolution of the projections is important for accurate delivery and controlling the dissolution rate will assist in cell targeting. Cryo-SEM data showed that in one example the projections start to dissolve immediately in skin as the projections become hydrated. Within one minute the projections have begun to dissolve and diffuse in the skin, anchoring and preventing them from being removed. The flexibility in the casting method facilitates the use of multiple materials which can be layered on the micron-scale within the projection molds. This accommodates the specific dissolution of multiple active compounds within individual projections in a single application.

Figure 17:
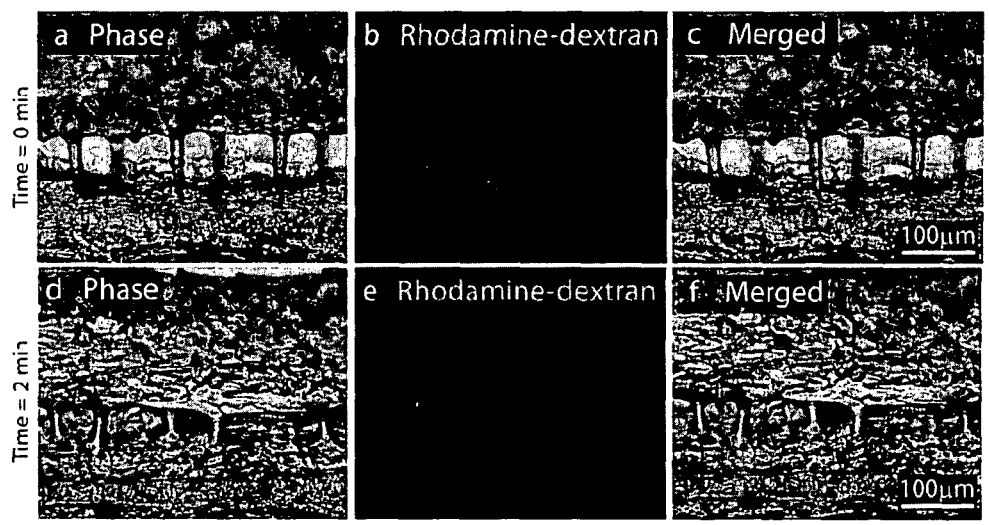
FIG. 17A to 17F shows images of a patch applied to murine skin to show dissolving of the projections.

Histology slices of a projection array applied to the skin verifies the results achieved with the CryoSEM. Snap-freezing at the time of application shows that the projections have penetrated the stratum corneum barrier and entered the skin, as shown in FIG. 17A to 17C. Two minutes after application, the projections have begun to dissolve and diffuse within the layers of the skin, as shown in FIGS. 17D to 17F. These results are consistent with the results achieved with the CryoSEM data with both experiments validating that the projections are able to penetrate and dissolve within the skin.

Figures 18A, 18B, 18C:
FIGS. 18A to 18C are images of a patch applied to murine skin to show dissolving of the projections five minutes after application.

Penetration and dissolution of the projections was also further confirmed by multiphoton microscopy, as shown in FIGS. 18A to 18C. Dermal penetration was verified by second harmonic generation of the dermal collagen surrounding the delivery sites of the projection. Analysis of the image using surface rendering based on fluorescent intensity clearly shows the collagen fibers with distinct payload delivery sites. The projections penetrated the skin resulting in the majority of the payload dissolving in the dermal region. The insert of FIG. 18C is a representative image showing a top view of the 3-dimensional image rendered with nine projection sites. Overall microscopy analysis of projection application shows that the projections can penetrate the skin and dissolve in a timely manner resulting in deposition sites of payload within the viable epidermis and dermis.

Figure 18D:
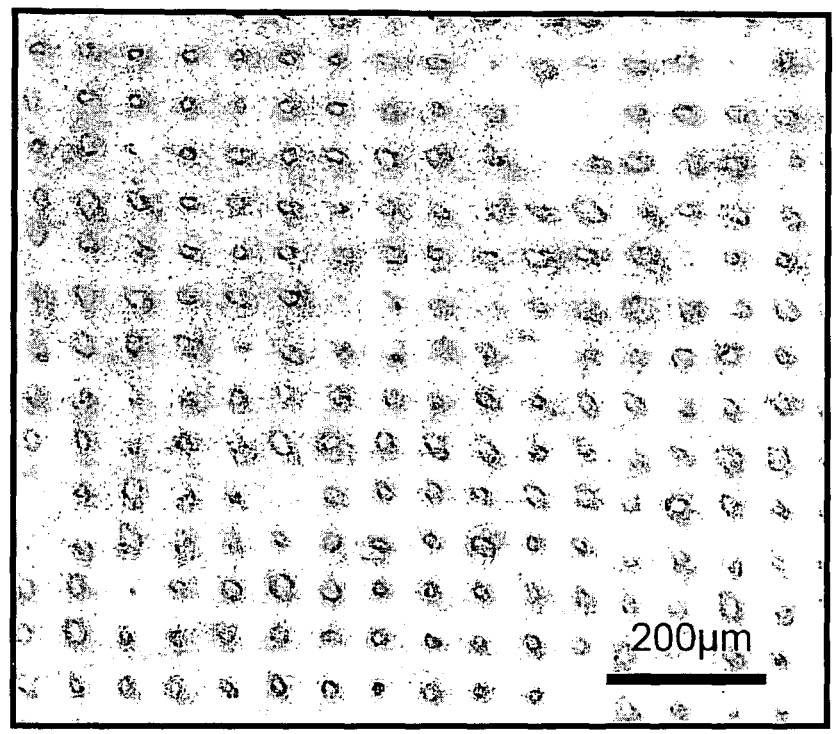
FIG. 18D is a confocal image showing the penetration of murine skin by projections.
Figure 18E:
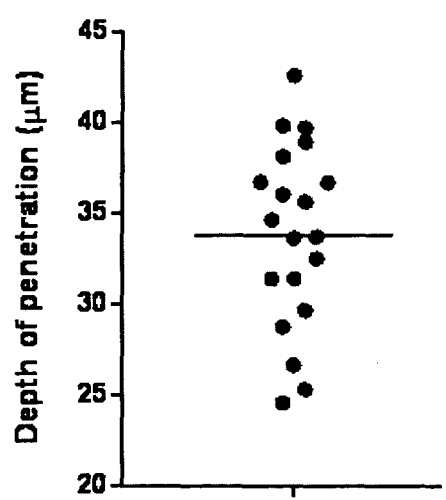
FIG. 18E is a graph showing the depth of penetration of murine skin by projections.

FIG. 18D is a confocal image showing the skin surface after application of the patch. This shows the penetration holes highlighting the successful penetration of the skin surface. The depth of penetration was further determined by measuring the distance from the surface of the skin to the depth of the projection fluorescence in the skin. A graph of results is shown in FIG. 18E, with each point on the graph representing the depth of penetration a single projection. This shows the projections penetrated through the epidermis and into the dermis resulting in a depth of penetration of 33.8 µm±5 µm.

In-vivo Delivery of Model Vaccine

Ovalbumin was used as a model vaccine to elicit an immune response in mice. The projection system consisted of dual layers with the active compound localized to the shafts, and excipient without payload in the backing layer. This was important in preventing any wastage of excess ovalbumin during production and application.

Female C57 black mice were anesthetized with an intraperitoneal injection of 1504 of 10 mg/mL ketamine and 2 mg/mL xylazil in sodium chloride. A dissolving ovalbumin projection array was applied to the ventral side of the ear. A high and low dose (8 μg and 0.2 μg, respectively) was administered with an n=4.

Application was with a spring applicator at 1.9 ms$^{-1}$ for 10 minutes. After application, a second dissolving ovalbumin projection array was applied to the ventral side of the other ear. The positive control consisted of a 5 μL intramuscular injection containing 15 μg of vaccine formulation containing 0.8 mg/mL Quil-A (Brenntag Biosector), 67.7 μM ovalbumin (Sigma-Aldrich) and methylcellulose (Sigma-Aldrich). The negative control was a patch with no projections coated with 10 μL of vaccine formulation containing 0.8 mg/mL Quil-A (Brenntag Biosector), 67.7 μM ovalbumin (Sigma-Aldrich) and 10 mg/mL methylcellulose (Sigma-Aldrich). The negative control was applied using the same protocol as the dissolving ovalbumin projection arrays. Low dose dissolving ovalbumin projection arrays were applied using the same protocol as for the high dose.

Figure 19A:
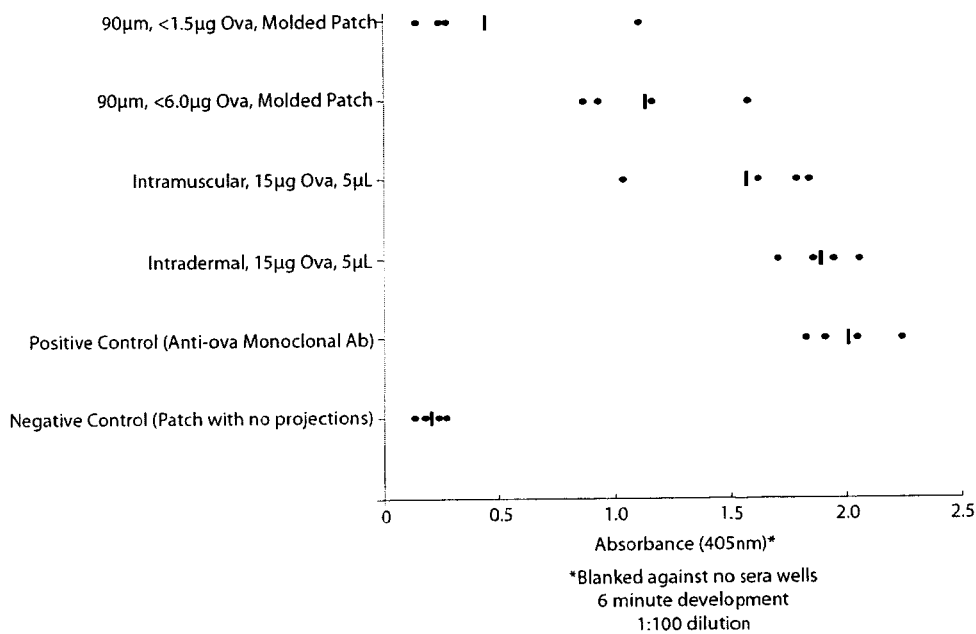
FIGS. 19A and 19B are graphs summarising ELISA results from after ovalbumin vaccination with multilayered dissolvable microneedles for 14 and 28 days respectively.
Figure 19B:
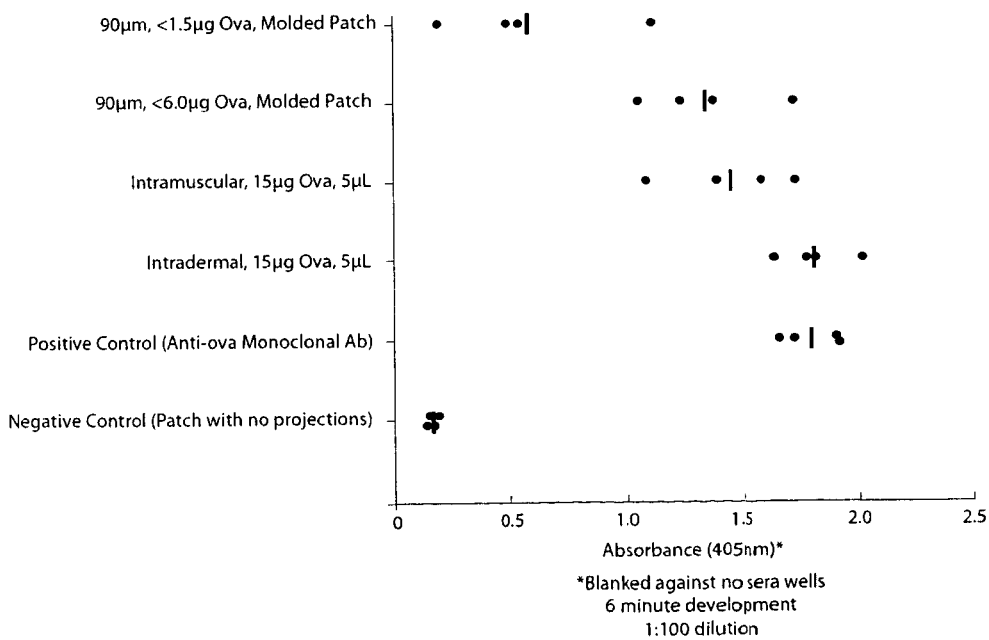

On day 14 and day 28 mice were bled. Approximately 100 μL of blood was taken from each mouse. The samples were centrifuged at 5000 g for 10 minutes to separate the blood from the sera. The sera were removed and stored at -80° C. for analysis. All that received the high dose of ovalbumin showed sero-conversion by day 14 with only one showing sero-conversion for the low dose, as shown in FIG. 19A. The high dose group showed sero-conversion at day 28 with antibody levels comparable to intramuscular injection, as shown in FIG. 19B.

Figure 20A:
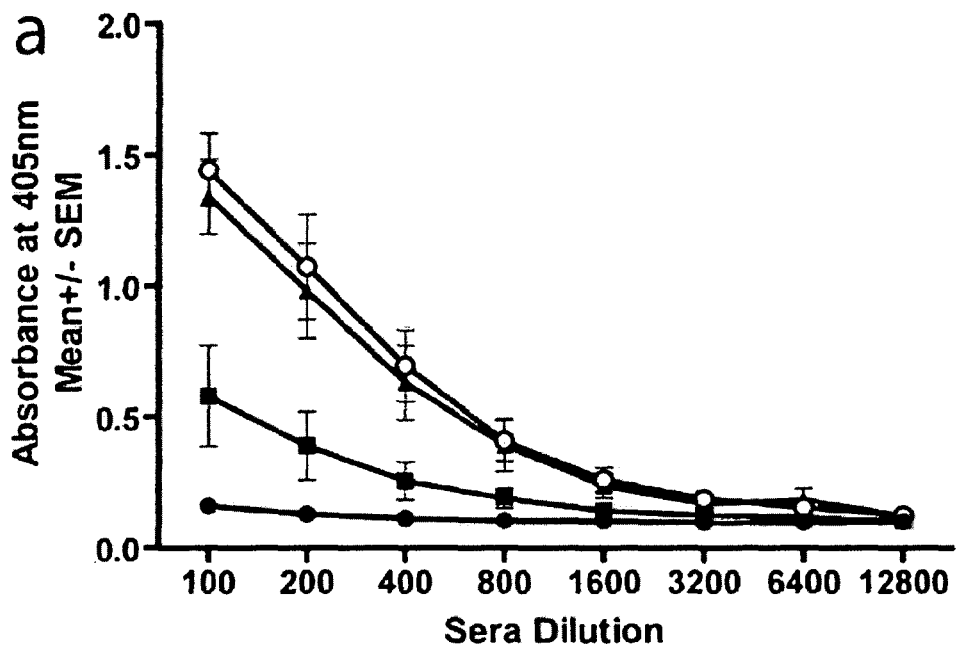
FIGS. 20A and 20B are graphs summarising ELISA results from after ovalbumin vaccination with multilayered dissolvable microneedles for 28 and 102 days respectively.
Figure 20B:
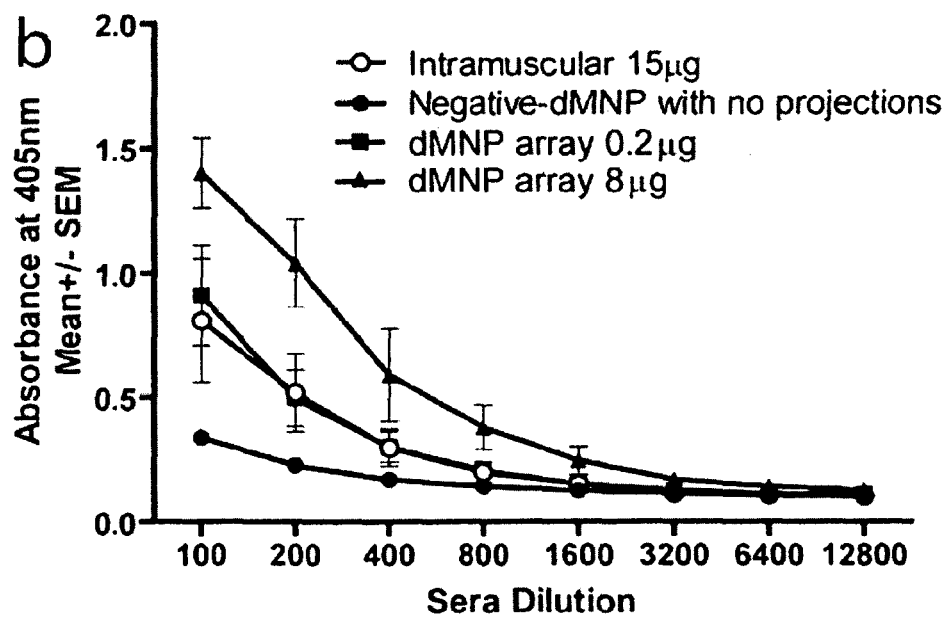

In a further similar study, mice were bled at 28 and 102 days, with the results being shown in FIGS. 20A and 20B. In this example, by day 28 the high dose group showed antibody levels comparable to the 15 μg intramuscular injection, as shown in FIG. 20A, whilst by day 102, the high dose group showed higher antibody levels than the intramuscular injection, with the low dose group showing comparable results, as shown in FIG. 20B.

Figure 21:
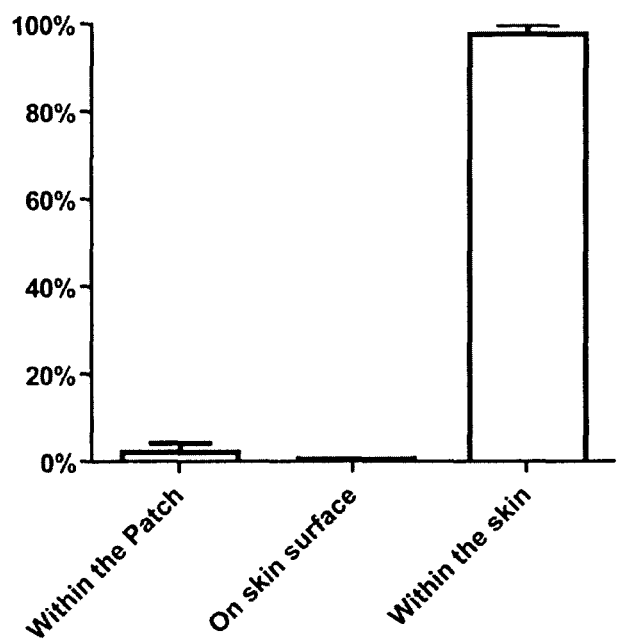
FIG. 21 is a graph of an example of the distribution of patch payload after delivery to murine skin.

In another further study, radio-labelled ovalbumin protein was cast into dissolving patches and applied to murine skin using a similar protocol, with the patches being retained in position for 5 minutes. The patches were removed and kept for analysis. The skin was swabbed post application and the swabs were kept for analysis. The skin was then excised and dissolved for analysis. The amount of radioactivity was counted, which directly relates to the amount of radio-labelled ovalbumin protein in each sample. The graph of FIG. 21 shows the distribution of payload in regards to what is actually delivered in the skin (98%), what remained on the surface (0.07%) and what remained in the patch (2%).

These results prove that a model protein antigen can be cast into a projection array and successfully delivered to immune cells in the skin, resulting in systemic antibody responses.

In-Vivo Delivery of Influenza Vaccine

Influenza was used to vaccinate mice using a commercial vaccine formulation.

Influenza vaccine formulation was concentrated to 0.5 mg/mL HA from Fluvax® (CSL Biotherapies) and 10 μL was pipetted onto the surface of the molds. Fluvax loaded molds were then centrifuged at 3000 g for 10 minutes. Excess formulation which had moved around the mold during centrifugation was reapplied to the surface of the mold. Molds were then centrifuged again at 3000 g for 10 minutes to allow further compaction and drying. A viscous solution containing 1.4 mM CMC was then added to the molds to provide the array backing layer. The molds were then centrifuged at 3000 g for 20 minutes. The molds were then placed in a sealed desiccator at 22° C., until the formulation had dried. The dissolving projection array was then removed from the molds and stored in a sealed desiccator at 4° C. until vaccination.

Female C57 black mice were anesthetized with an intraperitoneal injection of 1504 of 10 mg/mL ketamine and 2 mg/mL xylazil in sodium chloride. Each group contained four mice. A dissolving influenza projection array was applied to the ventral side of the ear. Administration was with a spring applicator at 1.9 ms$^{-1}$ for 10 minutes. After application, a second dissolving influenza projection array was applied to the ventral side of the other ear for one group only. The positive control consisted of a 5 μL intramuscular injection of vaccine formulation containing 0.5 μg and 5 μg influenza vaccine respectively. The negative control was a patch with no projections coated with 10 μL of vaccine formulation containing approximately 5 μg of influenza. The negative control was applied using the same protocol as the dissolving ovalbumin projection arrays. On day 14 and day 28 mice were bled. Approximately 100 μL of blood was taken from each mouse. The samples were centrifuged at 5000 g for 10 minutes to separate the blood from the sera. The sera were removed and stored at -80° C. for analysis.

Figures 22A, 22B:
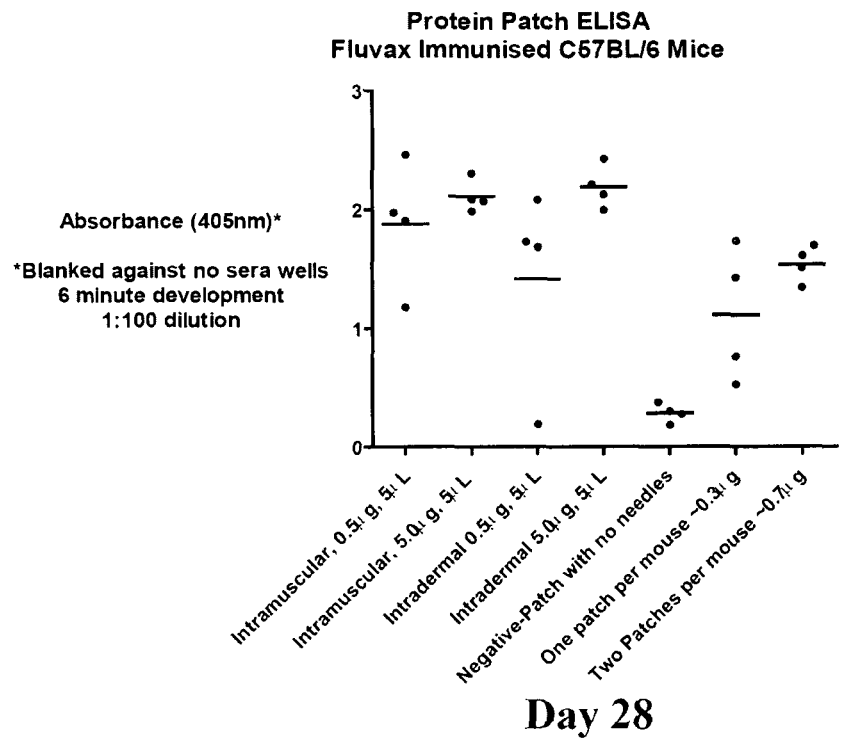
FIGS. 22A and 22B are graphs summarising ELISA results from after Fluvax vaccination with multilayered dissolvable microneedles for 14 and 28 days respectively.

The two-patch group showed sero-conversion by day 14 as shown in FIG. 22A. Two of four that received a single patch showed sero-conversion with two mice displaying antibody levels too low to confirm. Day 28 bleeds resulted in an increase in antibody levels of both patched groups, shown in FIG. 22B. By day 28 three of the four mice who received a single patch showed positive sero-conversion. The injection groups did not show any significant change in antibody levels.

Figure 23A:
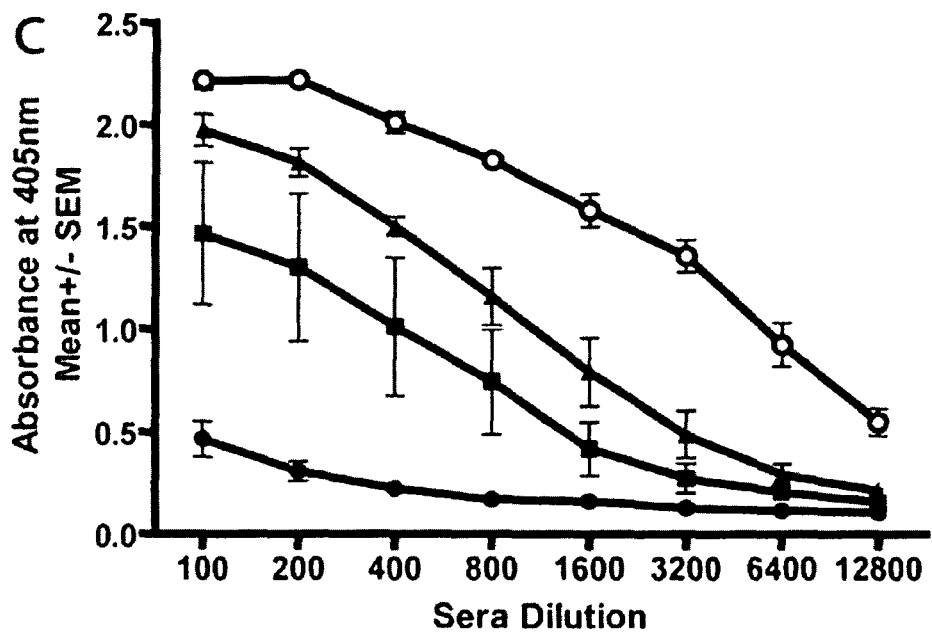
FIGS. 23A and 23B are graphs summarising ELISA results from after Fluvax vaccination with multilayered dissolvable microneedles for 28 and 102 days respectively; and, FIG. 24 is a graph of ELISPOT data showing results from immunization using different vaccines.
Figure 23B:
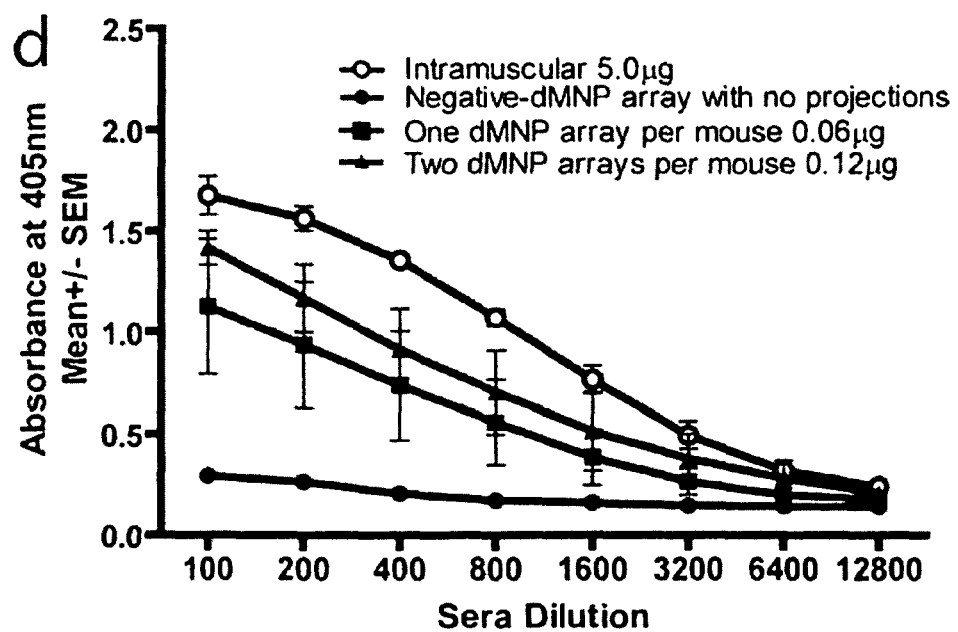

In a further similar study, mice were bled at 28 and 102 days, with the results being shown in FIGS. 23A and 23B. By day 28 both patched groups resulted in strong antibody responses, as shown in FIG. 23A. Similar to the ovalbumin immunization, antibody responses remained strong even at the day 102 bleed, as shown in FIG. 23B. These results verify the results achieved with the ovalbumin immunization and prove that the fabricated projection patches can deliver commercial vaccines to the skin.

Figure 24:
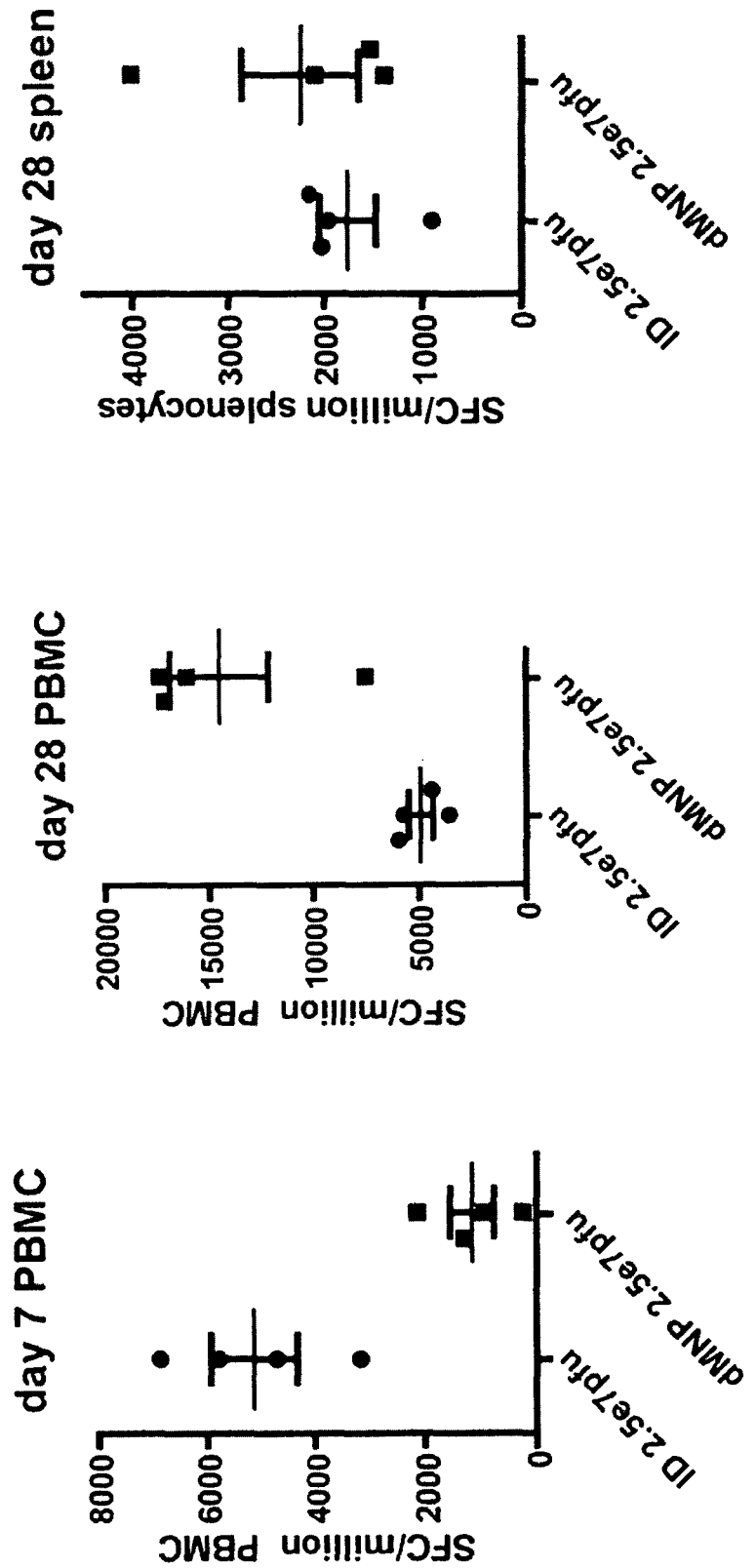

In another similar vaccination study, MVA.PbCSP immunisation of BalbC mice was performed using projection patches with ELISPOT data results being shown in FIG. 24. This includes results for a modified vaccine virus Ankara plasmodium berghei circumsporozoite protein (MVA.PbCSP) immunization in the murine model. MVA.PbCSP is an experimental vaccine for malaria. Mice are primed with either patch or intradermal administration with both conditions receiving an intradermal boost. The patch consisted of dual layers with MVA.PbCSP concentrated within the projections and a carboxymethylcellulose backing containing no active. Again, this demonstrates that projection patches can successfully deliver vaccines.

The current most common technique of vaccine administration is intramuscular injection using a needle and syringe. However, the above results show that the immune responses achieved with the projection patches required less antigen than the intramuscular injections. This is largely due to the difference in site of delivery between the two administration techniques. Intramuscular needle and syringe immunization targets deep muscle tissue and therefore requires relatively large amounts of vaccine to produce an immunological response. In contrast, the projection patches deliver vaccines directly to the skin, which contains an abundance of potent immunological cells, unlike the site of intramuscular injections. The ability to target key immune cells in the skin with the dissolving projections allows an immunological response to be achieved with minimal amounts of vaccine, making it ideal for vaccine delivery.

Accordingly, the above described technique allows for the creation of dissolving projections, as well as functional projections with layering on a micron scale. This allows for practical dose reduction in eliciting a desired response from a subject, as well as providing a mechanism for separating incompatible payloads in a single application, and incorporating multiple excipients to enhance rigidity or control payload release. The release of this payload is consequently controllable for each payload.

In particular, the process can controllably layer female molds of very small and densely packed micro/nano projections. In one example, female micro/nano projection molds are layered by dispersing the payload solution over the surface of the mold using a dispersion membrane. The mold is then centrifuged to evenly force the solution into the tips. The solution is dried and additional layers can be added using the same technique. The layering size can be controlled by solution, volume, concentration and centrifugation.

In another example, micro/nano projection molds consist of a base comprised of a semi-permeable membrane. Female micro/nano projection molds are layered by dispersing the payload solution over the surface of the mold using a dispersion membrane. The mold is then centrifuged to evenly force the solution into the tips. The semi-permeable membrane facilitates rapid drying. Water passes through the membrane but the payload remains in the mold. The solution is dried and additional layers can be added using the same technique. The layering size can be controlled by solution, volume, concentration and centrifugation.

In another example, female micro/nano projection molds are layered by dispersing the payload solution over the surface of the mold using a dispersion membrane. Different solvents are used to separate the layers and prevent diffusion within the mold. The mold is then centrifuged to evenly force the solution into the tips. Depending on the solvent's evaporation point, drying times can be controlled. The layering size can be controlled by solution, volume, concentration and centrifugation.

In one example, the layering solutions or gels can be prepared to contain incompatible payloads. The layering procedure can prevent the two payloads interacting with each other. In another example, insoluble compounds can be homogeneously distributed in a viscous layer. Because of the extremely high viscosity of media, the insoluble compounds will not precipitate out from layering media. Therefore, they can be layered in female micro/nano molds.

There is no limit to the size of the multilayered dissolvable needles desired. The methodology is scalable for projections from 10 μm to >5 mm in length with varying diameters, 1 μm to >1 mm. Likewise, there are no shape constraints for the projections.

The techniques can be applied to materials other than vaccines. In one example, it can be used to layer drugs into female micro/nano projections for drug delivery. In another embodiment, many immunological adjuvants can also be layered into micro/nano projections for delivery. In still another embodiment, virus like particles can be layered into female micro/nano projections for delivery.

Accordingly, the above described technique allows for accurate and uniform layering, controllable layering across all micro/nano projections, with minimal to no excess wastage of payload on the base of patches and the bottom part of micro/nano projections. The technique can avoid the reliance on particulate density for layering by drying in between layering and does not require heat to cast, therefore allowing for a broad range of biological compounds to be incorporated. It will be appreciated that the above described processes can also be implemented simply, flexibly and cost effectively due to no need for complex production equipment.

A number of further variations and options for use with the above described devices will now be described.

Herein, the terms "projection", "micro-nanoprojection", "nanoneedle", "nanoprojection", "needle", "rod" etc are used interchangeably to describe the projections.

A further feature is that the projections may be used for delivery not only through the skin but through other body surfaces, including mucosal surfaces, to cellular sites below the outer layer or layers of such surfaces. The term "internal site", as used herein, is to be understood as indicating a site below the outer layer(s) of skin and other tissues for which the devices of the present invention are to be used.

The device is suitable for intracellular delivery. The device is suitable for delivery to specific organelles within cells. Examples of organelles to which the device can be applied include a cell nucleus, or endoplasmic reticulum, for example.

In one example the device is provided having a needle support section, that is to say the projections comprise a suitable support section, of sufficient length to reach the desired site and a (needle) delivery end section having a length no greater than 20 microns and a maximum width no greater than 5 microns, preferably no greater than 2 microns.

In one example, the maximum width of the delivery end section is no greater than 1000 nm, even more preferably the maximum width of the delivery end section is no greater than 500 nm.

In a further example, the device is for mucosal delivery. This device may have a needle support section, that is to say the projections comprise a suitable support section, of sufficient length to reach the desired site, such as of length at least 100 microns and a (needle) delivery end section having a length no greater than 20 microns and a maximum width no greater than 5 microns, preferably no greater than 2 microns.

In one example, the device of the invention is for delivery to lung, eye, cornea, sclera or other internal organ or tissue. In a further example, the device is for in-vitro delivery to tissue, cell cultures, cell lines, organs, artificial tissues and tissue engineered products. This device typically has a needle support section, that is to say the projections comprise a suitable support section, of length at least 5 microns and a needle delivery end section having a length no greater than 20 microns and a maximum width no greater than 5 microns, preferably no greater than 2 microns.

In one example, the device comprises projections in which the (needle) delivery end section and support length, that is to say the "needle support section", contain a bioactive material across the whole or part of its length. The (needle) delivery end section and support length may be layered so that they contain material in selective areas thereof. This may depend upon the bioactive material being used or the target selected for example.

In a further example, a bioactive material is releasably incorporated into the material of which the needle, or projection, is composed. All, or part of the projection may be constructed of a biocompatible, biodegradable polymer (such as Poly Lactic Acid (PLA), PolyGlycolic Acid (PGA) or PGLA or Poly Glucleic Acid), which is formulated with the bioactive material of choice. The projections may then be inserted into the appropriate target site and, as they dissolve, the bioactive material will enter the organelle(s)/cells.

Examples of bioactive materials, which are not intended to be limiting with respect to the invention include polynucleotides and nucleic acid or protein molecules, antigens, allergens, adjuvants, molecules, elements or compounds. In addition, the device may contain materials such as biosensors, nanosensors or MEMS.

Illustrative material that can be delivered may include any or more of: small chemical or biochemical compounds including drugs, metabolites, amino acids, sugars, lipids, saponins, and hormones; macromolecules such as complex carbohydrates, phospholipids, peptides, polypeptides, peptidomimetics, and nucleic acids; or other organic (carbon containing) or inorganic molecules; and particulate matter including whole cells, bacteria, viruses, virus-like particles, cell membranes, dendrimers and liposomes.

The material can be selected from nucleic acids, illustrative examples of which include DNA, RNA, sense oligonucleotides, antisense oligonucleotides, ribozymes, small interfering oligonucleotides (siRNAs), micro RNAs (miRNAs), repeat associated RNAs (rasiRNA), effector RNAs (eRNAs), and any other oligonucleotides known in the art, which inhibit transcription and/or translation of a mutated or other detrimental protein. In illustrative examples of this type, the nucleic acid is in the form of an expression vector from which a polynucleotide of interest is expressible. The polynucleotide of interest may encode a polypeptide or an effector nucleic acid molecule such as sense or antisense oligonucleotides, siRNAs, miRNAs and eRNAs.

The material can be selected from peptides or polypeptides, illustrative examples of which include insulin, proinsulin, follicle stimulating hormone, insulin like growthfactor-1, insulin like growth factor-2, platelet derived growth factor, epidermal growth factor, fibroblast growth factors, nerve growth factor, colony stimulating factors, transforming growth factors, tumor necrosis factor, calcitonin, parathyroid hormone, growth hormone, bone morphogenic protein, erythropoietin, hemopoietic growth factors, luteinizing hormone, glucagon, glucagon likepeptide-1, anti-angiogenic proteins, clotting factors, anti-clotting factors, atrial natriuretic factor, plasminogen activators, bombesin, thrombin, enkephalinase, vascular endothelial growth factor, interleukins, viral antigens, non-viral antigens, transport proteins, and antibodies.

The material can be selected from receptor ligands. Illustrative examples of receptors include Fc receptor, heparin sulfate receptor, vitronectin receptor, Vcam-1 receptor, hemaglutinin receptor, Pvr receptor, Icam-1 receptor, decay-accelerating protein (CD55) receptor, Car (coxsackievirus-adenovirus) receptor, integrin receptor, sialic acid receptor, HAVCr-1 receptor, low-density lipoprotein receptor, BGP (biliary glycoprotien) receptor, aminopeptidease N receptor, MHC class-1 receptor, laminin receptor, nicotinic acetylcholine receptor, CD56 receptor, nerve growth factor receptor, CD46 receptor, asialoglycoprotein receptor Gp-2, alpha-dystroglycan receptor, galactosylceramide receptor, Cxcr4 receptor, Glvr1 receptor, Ram-1 receptor, Cat receptor, Tva receptor, BLVRcp1 receptor, MHC class-2 receptor, toll-like receptors (such as TLR-1 to -6) and complement receptors.

The material can be selected from antigens including endogenous antigens produced by a host that is the subject of the stimulus or material delivery or exogenous antigens that are foreign to that host. The antigens may be in the form of soluble peptides or polypeptides or polynucleotides from which an expression product (e.g., protein or RNA) is producible. Suitable endogenous antigens include, but are not restricted to, cancer or tumor antigens. Non-limiting examples of cancer or tumor antigens include antigens from a cancer or tumor selected from ABL1 proto-oncogene, AIDS related cancers, acoustic neuroma, acute lymphocytic leukemia, acute myeloid leukemia, adenocystic carcinoma, adrenocortical cancer, agnogenic myeloid metaplasia, alopecia, alveolar soft-part sarcoma, anal cancer, angiosarcoma, aplastic anemia, astrocytoma, ataxia-telangiectasia, basal cell carcinoma (skin), bladder cancer, bone cancers, bowel cancer, brain stem glioma, brain and CNS tumors, breast cancer, CNS tumors, carcinoid tumors, cervical cancer, childhood brain tumors, childhood cancer, childhood leukemia, childhood soft tissue sarcoma, chondrosarcoma, choriocarcinoma, chronic lymphocytic leukemia, chronic myeloid leukemia, colorectal cancers, cutaneous T-cell lymphoma, dermatofibrosarcoma protuberans, desmoplastic small round cell tumor, ductal carcinoma, endocrine cancers, endometrial cancer, ependymoma, oesophageal cancer, Ewing's Sarcoma, Extra-Hepatic Bile Duct Cancer, Eye Cancer, Eye: Melanoma, Retinoblastoma, Fallopian Tube cancer, Fanconi anemia, fibrosarcoma, gall bladder cancer, gastric cancer, gastrointestinal cancers, gastrointestinal-carcinoid-tumor, genitourinary cancers, germ cell tumors, gestational-trophoblastic-disease, glioma, gynecological cancers, haematological malignancies, hairy cell leukemia, head and neck cancer, hepatocellular cancer, hereditary breast cancer, histiocytosis, Hodgkin's disease, human papillomavirus, hydatidiform mole, hypercalcemia, hypopharynx cancer, intraocular melanoma, islet cell cancer, Kaposi's sarcoma, kidney cancer, Langerhan's cell histiocytosis, laryngeal cancer, leiomyosarcoma, leukemia, Li-Fraumeni syndrome, lip cancer, liposarcoma, liver cancer, lung cancer, lymphedema, lymphoma, Hodgkin's lymphoma, non-Hodgkin's lymphoma, male breast cancer, malignant-rhabdoid tumor of kidney, medulloblastoma, melanoma, Merkel cell cancer, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, Nijmegen breakage syndrome, non-melanoma skin cancer, non-small-cell-lung-cancer (NSCLC), ocular cancers, esophageal cancer, oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal tumours, pituitary cancer, polycythemia vera, prostate cancer, rare cancers and associated disorders, renal cell carcinoma, retinoblastoma, rhabdomyosarcoma, Rothmund-Thomson syndrome, salivary gland cancer, sarcoma, schwannoma, Sezary syndrome, skin cancer, small cell lung cancer (SCLC), small intestine cancer, soft tissue sarcoma, spinal cord tumors, squamous-cell-carcinoma-(skin), stomach cancer, synovial sarcoma, testicular cancer, thymus cancer, thyroid cancer, transitional-cell-cancer-(bladder), transitional-cell-cancer-(renal-pelvis-/-ureter), trophoblastic cancer, urethral cancer, urinary system cancer, uroplakins, uterine sarcoma, uterus cancer, vaginal cancer, vulva cancer, Waldenstrom's macroglobulinemia, Wilms' tumor. In certain examples, the cancer or tumor relates to melanoma. Illustrative examples of melanoma-related antigens include melanocyte differentiation antigen (e.g., gp100, MART, Melan-A/MART-1, TRP-1, Tyros, TRP2, MC1R, MUC1F, MUC1R or a combination thereof) and melanoma-specific antigens (e.g., BAGE, GAGE-1, gp100In4, MAGE-1 (e.g., GenBank Accession No. X54156 and AA494311), MAGE-3, MAGE4, PRAME, TRP2IN2, NYNSO1a, NYNSO1b, LAGE1, p97 melanoma antigen (e.g., GenBank Accession No. M12154) p5 protein, gp75, oncofetal antigen, GM2 and GD2 gangliosides, cdc27, p21ras, gp100$^{PMEL117}$ or a combination thereof. Other tumour-specific antigens include, but are not limited to: etv6, aml1, cyclophilin b (acute lymphoblastic leukemia); Ig-idiotype (B cell lymphoma); E-cadherin, α-catenin, β-catenin, γ-catenin, p120ctn (glioma); p21ras (bladder cancer); p21ras (biliary cancer); MUC family, HER2/neu, c-erbB-2 (breast cancer); p53, p21ras (cervical carcinoma); p21ras, HER2/neu, c-erbB-2, MUC family, Cripto-1protein, Pim-1 protein (colon carcinoma); Colorectal associated antigen (CRC)-CO17-1A/GA733, APC (colorectal cancer); carcinoembryonic antigen (CEA) (colorectal cancer; choriocarcinoma); cyclophilin b (epithelial cell cancer); HER2/neu, c-erbB-2, ga733 glycoprotein (gastric cancer); α-fetoprotein (hepatocellular cancer); Imp-1, EBNA-1 (Hodgkin's lymphoma); CEA, MAGE-3, NY-ESO-1 (lung cancer); cyclophilin b (lymphoid cell-derived leukemia); MUC family, p21ras (myeloma); HER2/neu, c-erbB-2 (non-small cell lung carcinoma); Imp-1, EBNA-1 (nasopharyngeal cancer); MUC family, HER2/neu, c-erbB-2, MAGE-A4, NY-ESO-1 (ovarian cancer); Prostate Specific Antigen (PSA) and its antigenic epitopes PSA-1, PSA-2, and PSA-3, PSMA, HER2/neu, c-erbB-2, ga733 glycoprotein (prostate cancer); HER2/neu, c-erbB-2 (renal cancer); viral products such as human papillomavirus proteins (squamous cell cancers of the cervix and esophagus); NY-ESO-1 (testicular cancer); and HTLV-1 epitopes (T cell leukemia).

Foreign antigens are suitably selected from transplantation antigens, allergens as well as antigens from pathogenic organisms. Transplantation antigens can be derived from donor cells or tissues from e.g., heart, lung, liver, pancreas, kidney, neural graft components, or from the donor antigen-presenting cells bearing MHC loaded with self antigen in the absence of exogenous antigen.

Non-limiting examples of allergens include Fel d 1 (i.e., the feline skin and salivary gland allergen of the domestic cat *Felis domesticus*, the amino acid sequence of which is disclosed International Publication WO 91/06571), Der p I, Der p II, Der fI or Der fII (i.e., the major protein allergens from the house dust mite dermatophagoides, the amino acid sequence of which is disclosed in International Publication WO 94/24281). Other allergens may be derived, for example from the following: grass, tree and weed (including ragweed) pollens; fungi and molds; foods such as fish, shellfish, crab, lobster, peanuts, nuts, wheat gluten, eggs and milk; stinging insects such as bee, wasp, and hornet and the chirnomidae (non-biting midges); other insects such as the housefly, fruit-fly, sheep blow fly, screw worm fly, grain weevil, silkworm, honeybee, non-biting midge larvae, bee moth larvae, mealworm, cockroach and larvae of *Tenibrio molitor* beetle; spiders and mites, including the house dust mite; allergens found in the dander, urine, saliva, blood or other bodily fluid of mammals such as cat, dog, cow, pig, sheep, horse, rabbit, rat, guinea pig, mouse and gerbil; airborne particulates in general; latex; and protein detergent additives.

The material can be pathogenic organisms such as, but are not limited to, viruses, bacteria, fungi parasites, algae and protozoa and amoebae. Illustrative viruses include viruses responsible for diseases including, but not limited to, measles, mumps, rubella, poliomyelitis, hepatitis A, B (e.g., GenBank Accession No. E02707), and C (e.g., GenBank Accession No. E06890), as well as other hepatitis viruses, influenza, adenovirus (e.g., types 4 and 7), rabies (e.g., GenBank Accession No. M34678), yellow fever, Epstein-Barr virus and other herpesviruses such as papillomavirus, Ebola virus, Chikungunya virus, influenza virus, Japanese encephalitis (e.g., GenBank Accession No. E07883), dengue (e.g., GenBank Accession No. M24444), hantavirus, Sendai virus, respiratory syncytial virus, othromyxoviruses, vesicular stomatitis virus, visna virus, cytomegalovirus and human immunodeficiency virus (HIV) (e.g., GenBank Accession No. U18552). Any suitable antigen derived from such viruses are useful in the practice of the present invention. For example, illustrative retroviral antigens derived from HIV include, but are not limited to, antigens such as gene products of the gag, pol, and env genes, the Nef protein, reverse transcriptase, and other HIV components. Illustrative examples of hepatitis viral antigens include, but are not limited to, antigens such as the S, M, and L proteins of hepatitis B virus, the pre-S antigen of hepatitis B virus, and other hepatitis, e.g., hepatitis A, B, and C, viral components such as hepatitis C viral RNA. Illustrative examples of influenza viral antigens include; but are not limited to, antigens such as hemagglutinin and neurarninidase and other influenza viral components. Illustrative examples of measles viral antigens include, but are not limited to, antigens such as the measles virus fusion protein and other measles virus components. Illustrative examples of rubella viral antigens include, but are not limited to, antigens such as proteins E1 and E2 and other rubella virus components; rotaviral antigens such as VP7sc and other rotaviral components. Illustrative examples of cytomegaloviral antigens include, but are not limited to, antigens such as envelope glycoprotein B and other cytomegaloviral antigen components. Non-limiting examples of respiratory syncytial viral antigens include antigens such as the RSV fusion protein, the M2 protein and other respiratory syncytial viral antigen components. Illustrative examples of herpes simplex viral antigens include, but are not limited to, antigens such as immediate early proteins, glycoprotein D, and other herpes simplex viral antigen components. Non-limiting examples of varicella zoster viral antigens include antigens such as 9PI, gpII, and other varicella zoster viral antigen components. Non-limiting examples of Japanese encephalitis viral antigens include antigens such as proteins E, M-E, M-E-NS 1, NS 1, NS 1-NS2A, 80% E, and other Japanese encephalitis viral antigen components. Representative examples of rabies viral antigens include, but are not limited to, antigens such as rabies glycoprotein, rabies nucleoprotein and other rabies viral antigen components. Illustrative examples of papillomavirus antigens include, but are not limited to, the L1 and L2 capsid proteins as well as the E6/E7 antigens associated with cervical cancers, See Fundamental Virology, Second Edition, eds. Fields, B. N. and Knipe, D. M., 1991, Raven Press, New York, for additional examples of viral antigens.

Illustrative examples of fungi include *Acremonium* spp., *Aspergillus* spp., *Basidiobolus* spp., *Bipolaris* spp., *Blastomyces dermatidis*, *Candida* spp., *Cladophialophora carrionii*, *Coccoidiodes immitis*, *Conidiobolus* spp., *Cryptococcus* spp., *Curvularia* spp., *Epidermophyton* spp., *Exophiala jeanselmei*, *Exserohilum* spp., *Fonsecaea compacta*, *Fonsecaea pedrosoi*, *Fusarium oxysporum*, *Fusarium solani*, *Geotrichum candidum*, *Histoplasma capsulatum* var. *capsulatum*, *Histoplasma capsulatum* var. *duboisii*, *Hortaea werneckii*, *Lacazia loboi*, *Lasiodiplodia theobromae*, *Leptosphaeria senegalensis*, *Madurella grisea*, *Madurella mycetomatis*, *Malassezia furfur*, *Microsporum* spp., *Neotestudina rosatii*, *Onychocola canadensis*, *Paracoccidioides brasiliensis*, *Phialophora verrucosa*, *Piedraia hortae*, *Piedra iahortae*, *Pityriasis versicolor*, *Pseudallesheria boydii*, *Pyrenochaeta romeroi*, *Rhizopus arrhizus*, *Scopulariopsis brevicaulis*, *Scytalidium dimidiatum*, *Sporothrix schenckii*, *Trichophyton* spp., *Trichosporon* spp., *Zygomcete fungi*, *Absidia corymbifera*, *Rhizomucor pusillus* and *Rhizopus arrhizus*. Thus, representative fungal antigens that can be used in the compositions and methods of the present invention include, but are not limited to, candida fungal antigen components; histoplasma fungal antigens such as heat shock protein 60 (HSP60) and other histoplasma fungal antigen components; cryptococcal fungal antigens such as capsular polysaccharides and other cryptococcal fungal antigen components; coccidiodes fungal antigens such as spherule antigens and other coccidiodes fungal antigen components; and tinea fungal antigens such as trichophytin and other coccidiodes fungal antigen components.

Illustrative examples of bacteria include bacteria that are responsible for diseases including, but not restricted to, diphtheria (e.g., *Corynebacterium diphtheria*), pertussis (e.g., *Bordetella pertussis*, GenBank Accession No. M35274), tetanus (e.g., *Clostridium tetani*, GenBank Accession No. M64353), tuberculosis (e.g., *Mycobacterium tuberculosis*), bacterial pneumonias (e.g., *Haemophilus influenzae*.), cholera (e.g., *Vibrio cholerae*), anthrax (e.g., *Bacillus anthracis*), typhoid, plague, shigellosis (e.g., *Shigella dysenteriae*), botulism (e.g., *Clostridium botulinum*), salmonellosis (e.g., GenBank Accession No. L03833), peptic ulcers (e.g., *Helicobacter pylori*), Legionnaire's Disease, Lyme disease (e.g., GenBank Accession No. U59487), Other pathogenic bacteria include *Escherichia coli, Clostridium perfringens, Pseudomonas aeruginosa, Staphylococcus aureus* and *Streptococcus pyogenes*. Thus, bacterial antigens which can be used in the compositions and methods of the invention include, but are not limited to: pertussis bacterial antigens such as pertussis toxin, filamentous hemagglutinin, pertactin, F M2, FIM3, adenylate cyclase and other pertussis bacterial antigen components; diphtheria bacterial antigens such as diphtheria toxin or toxoid and other diphtheria bacterial antigen components; tetanus bacterial antigens such as tetanus toxin or toxoid and other tetanus bacterial antigen components, streptococcal bacterial antigens such as M proteins and other streptococcal bacterial antigen components; gram-negative bacilli bacterial antigens such as lipopolysaccharides and other gram-negative bacterial antigen components; *Mycobacterium tuberculosis* bacterial antigens such as mycotic acid, heat shock protein 65 (HSP65), the kDa major secreted protein, antigen 85A and other mycobacterial antigen components; *Helicobacter pylori* bacterial antigen components, pneumococcal bacterial antigens such as pneumolysin, pneumococcal capsular polysaccharides and other pnermiococcal bacterial antigen components; *Haemophilus influenza* bacterial antigens such as capsular polysaccharides and other *Haemophilus influenza* bacterial antigen components; anthrax bacterial antigens such as anthrax protective antigen and other anthrax bacterial antigen components; rickettsiae bacterial antigens such as rompA and other rickettsiae bacterial antigen component. Also included with the bacterial antigens described herein are any other bacterial, mycobacterial, mycoplasmal, rickettsial, or chlamydial antigens.

Illustrative examples of protozoa include protozoa that are responsible for diseases including, but not limited to, malaria (e.g., GenBank Accession No. X53832), hookworm, onchocerciasis (e.g., GenBank Accession No. M27807), schistosomiasis (e.g., GenBank Accession No. LOS 198), toxoplasmosis, trypanosomiasis, leishmaniasis, giardiasis (GenBank Accession No. M33641), amoebiasis, filariasis (e.g., GenBank Accession No. J03266), borreliosis, and trichinosis. Thus, protozoal antigens which can be used in the compositions and methods of the invention include, but are not limited to: plasmodium falciparum antigens such as merozoite surface antigens, sporozoite surface antigens, circumsporozoite antigens, gametocyte/gamete surface antigens, blood-stage antigen pf 155/RESA and other plasmodial antigen components; toxoplasma antigens such as SAG-1, p30 and other toxoplasmal antigen components; schistosomae antigens such as glutathione-S-transferase, paramyosin, and other schistosomal antigen components; *leishmania major* and other leishmaniae antigens such as gp63, lipophosphoglycan and its associated protein and other leishmanial antigen components; and *trypanosoma cruzi* antigens such as the 75-77 kDa antigen, the 56 kDa antigen and other trypanosomal antigen components.

The material can be toxin components acting as antigens. Illustrative examples of toxins include, but are not restricted to, staphylococcal enterotoxins, toxic shock syndrome toxin; retroviral antigens (e.g., antigens derived from HIV), streptococcal antigens, staphylococcal enterotoxin-A (SEA), staphylococcal enterotoxin-B (SEB), staphylococcal enterotoxin$_{1-3}$ (SE$_{1-3}$), staphylococcal enterotoxin-D (SED), staphylococcal enterotoxin-E (SEE) as well as toxins derived from mycoplasma, mycobacterium, and herpes viruses.

In specific examples, the antigen is delivered to antigen-presenting cells. Such antigen-presenting cells include professional or facultative antigen-presenting cells. Professional antigen-presenting cells function physiologically to present antigen in a form that is recognised by specific T cell receptors so as to stimulate or anergise a T lymphocyte or B lymphocyte mediated immune response. Professional antigen-presenting cells not only process and present antigens in the context of the major histocompatability complex (MHC), but also possess the additional immunoregulatory molecules required to complete T cell activation or induce a tolerogenic response. Professional antigen-presenting cells include, but are not limited to, macrophages, monocytes, B lymphocytes, cells of myeloid lineage, including monocytic-granulocytic-DC precursors, marginal zone Kupffer cells, microglia, T cells, Langerhans cells and dendritic cells including interdigitating dendritic cells and follicular dendritic cells. Non-professional or facultative antigen-presenting cells typically lack one or more of the immunoregulatory molecules required to complete T lymphocyte activation or anergy. Examples of non-professional or facultative antigen-presenting cells include, but are not limited to, activated T lymphocytes, eosinophils, keratinocytes, astrocytes, follicular cells, microglial cells, thymic cortical cells, endothelial cells, Schwann cells, retinal pigment epithelial cells, myoblasts, vascular smooth muscle cells, chondrocytes, enterocytes, thymocytes, kidney tubule cells and fibroblasts. In some examples, the antigen-presenting cell is selected from monocytes, macrophages, B lymphocytes, cells of myeloid lineage, dendritic cells or Langerhans cells. In certain advantageous examples, the antigen-presenting cell expresses CD11c and includes a dendritic cell or Langerhans cell. In some examples the antigen-presenting cell stimulates an immune response. In other examples, the antigen-presenting cell induces a tolerogenic response.

The delivery of exogenous antigen to an antigen-presenting cell can be enhanced by methods known to practitioners in the art. For example, several different strategies have been developed for delivery of exogenous antigen to the endogenous processing pathway of antigen-presenting cells, especially dendritic cells. These methods include insertion of antigen into pH-sensitive liposomes (Zhou and Huang, 1994, *Immunomethods*, 4:229-235), osmotic lysis of pinosomes after pinocytic uptake of soluble antigen (Moore et al., 1988, *Cell*, 54:777-785), coupling of antigens to potent adjuvants (Aichele et al., 1990, *J. Exp. Med.*, 171: 1815-1820; Gao et al., 1991, *J. Immunol.*, 147: 3268-3273; Schulz et al., 1991, *Proc. Natl. Acad. Sci. USA*, 88: 991-993; Kuzu et al., 1993, *Euro. J. Immunol.*, 23: 1397-1400; and Jondal et al., 1996, *Immunity* 5: 295-302) and apoptotic cell delivery of antigen (Albert et al. 1998, *Nature* 392:86-89; Albert et al. 1998, *Nature Med.* 4:1321-1324; and in International Publications WO 99/42564 and WO 01/85207). Recombinant bacteria (eg. *E. coli*) or transfected host mammalian cells may be pulsed onto dendritic cells (as particulate antigen, or apoptotic bodies respectively) for antigen delivery. Recombinant chimeric virus-like particles (VLPs) have also been used as vehicles for delivery of exogenous heterologous antigen to the MHC class I processing pathway of a dendritic cell line (Bachmann et al., 1996, *Eur. J. Immunol.*, 26(11): 2595-2600).

Alternatively, or in addition, an antigen may be linked to, or otherwise associated with, a cytolysin to enhance the transfer of the antigen into the cytosol of an antigen-presenting cell of the invention for delivery to the MHC class I pathway. Exemplary cytolysins include saponin compounds such as saponin-containing Immune Stimulating Complexes (ISCOMs) (see e.g., Cox and Coulter, 1997, *Vaccine* 15(3): 248-256 and U.S. Pat. No. 6,352,697), phospholipases (see, e.g., Camilli et al., 1991, *J. Exp. Med.* 173: 751-754), pore-forming toxins (e.g., an α-toxin), natural cytolysins of gram-positive bacteria, such as listeriolysin O (LLO, e.g., Mengaud et al., 1988, *Infect. Immun.* 56: 766-772 and Portnoy et al., 1992, *Infect. Immun.* 60: 2710-2717), streptolysin O (SLO, e.g., Palmer et al., 1998, *Biochemistry* 37(8): 2378-2383) and perfringolysin O (PFO, e.g., Rossjohn et al., *Cell* 89(5): 685-692). Where the antigen-presenting cell is phagosomal, acid activated cytolysins may be advantageously used. For example, listeriolysin exhibits greater pore-forming ability at mildly acidic pH (the pH conditions within the phagosome), thereby facilitating delivery of vacuole (including phagosome and endosome) contents to the cytoplasm (see, e.g., Portnoy et al., *Infect. Immun.* 1992, 60: 2710-2717).

The cytolysin may be provided together with a pre-selected antigen in the form of a single composition or may be provided as a separate composition, for contacting the antigen-presenting cells. In one example, the cytolysin is fused or otherwise linked to the antigen, wherein the fusion or linkage permits the delivery of the antigen to the cytosol of the target cell. In another example, the cytolysin and antigen are provided in the form of a delivery vehicle such as, but not limited to, a liposome or a microbial delivery vehicle selected from virus, bacterium, or yeast. Suitably, when the delivery vehicle is a microbial delivery vehicle, the delivery vehicle is non-virulent. In a preferred example of this type, the delivery vehicle is a non-virulent bacterium, as for example described by Portnoy et al. in U.S. Pat. No. 6,287,556, comprising a first polynucleotide encoding a non-secreted functional cytolysin operably linked to a regulatory polynucleotide which expresses the cytolysin in the bacterium, and a second polynucleotide encoding one or more pre-selected antigens. Non-secreted cytolysins may be provided by various mechanisms, e.g., absence of a functional signal sequence, a secretion incompetent microbe, such as microbes having genetic lesions (e.g., a functional signal sequence mutation), or poisoned microbes, etc. A wide variety of nonvirulent, non-pathogenic bacteria may be used; preferred microbes are relatively well characterised strains, particularly laboratory strains of *E. coli*, such as MC4100, MC1061, DH5α, etc. Other bacteria that can be engineered for the invention include well-characterised, nonvirulent, non-pathogenic strains of *Listeria monocytogenes, Shigella flexneri*, mycobacterium, *Salmonella, Bacillus subtilis*, etc. In a particular example, the bacteria are attenuated to be non-replicative, non-integrative into the host cell genome, and/or non-motile inter- or intra-cellularly.

The dissolving multi-layered projections described above can be used to deliver one or more antigens to virtually any antigen-presenting cell capable of endocytosis of the subject vehicle, including phagocytic and non-phagocytic antigen-presenting cells. In examples when the delivery vehicle is a microbe, the subject methods generally require microbial uptake by the target cell and subsequent lysis within the antigen-presenting cell vacuole (including phagosomes and endosomes).

In other examples, the antigen is produced inside the antigen-presenting cell by introduction of a suitable expression vector as for example described above. The antigen-encoding portion of the expression vector may comprise a naturally-occurring sequence or a variant thereof, which has been engineered using recombinant techniques. In one example of a variant, the codon composition of an antigen-encoding polynucleotide is modified to permit enhanced expression of the antigen in a target cell or tissue of choice using methods as set forth in detail in International Publications WO 99/02694 and WO 00/42215. Briefly, these methods are based on the observation that translational efficiencies of different codons vary between different cells or tissues and that these differences can be exploited, together with codon composition of a gene, to regulate expression of a protein in a particular cell or tissue type. Thus, for the construction of codon-optimised polynucleotides, at least one existing codon of a parent polynucleotide is replaced with a synonymous codon that has a higher translational efficiency in a target cell or tissue than the existing codon it replaces. Although it is preferable to replace all the existing codons of a parent nucleic acid molecule with synonymous codons which have that higher translational efficiency, this is not necessary because increased expression can be accomplished even with partial replacement. Suitably, the replacement step affects 5, 10, 15, 20, 25, 30%, more preferably 35, 40, 50, 60, 70% or more of the existing codons of a parent polynucleotide.

The expression vector for introduction into the antigen-presenting cell will be compatible therewith such that the antigen-encoding polynucleotide is expressible by the cell. For example, expression vectors of this type can be derived from viral DNA sequences including, but not limited to, adenovirus, adeno-associated viruses, herpes-simplex viruses and retroviruses such as B, C, and D retroviruses as well as spumaviruses and modified lentiviruses. Suitable expression vectors for transfection of animal cells are described, for example, by Wu and Ataai (2000, *Curr. Opin. Biotechnol.* 11(2):205-208), Vigna and Naldini (2000, *J. Gene Med.* 2(5): 308-316), Kay, et al. (2001, *Nat. Med.* 7(1):33-40), Athanasopoulos, et al. (2000, *Int. J. Mol. Med.* 6(4):363-375) and Walther and Stein (2000, *Drugs* 60(2):249-271).

In one aspect, the device is provided in the form of a patch containing a plurality of needles (projections) for application to a body surface. A multiplicity of projections can allow multiple cells and organelles to be targeted and provided with a material at the same time. The patch may be of any suitable shape, such as square or round for example. The overall number of projections per patch depends upon the particular application in which the device is to be used. Preferably, the patch has at least 10 needles per mm, and more preferably at least 100 needles per $mm^2$. Considerations and specific examples of such a patch are provided in more detail below.

Examples of specific manufacturing steps used to fabricate the device are described in greater detail above. In one preferred aspect, the device of the invention is constructed from biocompatible materials such as Titanium, Gold, Silver or Silicon, for example. This may be the entire device, or alternatively it may only be the projections or the delivery end section of the projections which are made from the biocompatible materials.

Persons skilled in the art will appreciate that numerous variations and modifications will become apparent. All such variations and modifications which become apparent to persons skilled in the art, should be considered to fall within the spirit and scope that the invention broadly appearing before described.

The claims defining the invention are as follows:
1. A method for use in producing a patch having a number of projections thereon, the method including:
   a) providing a distribution member and filling material on a mold surface of a mold, the mold including a number of cavities extending from the mold surface for defining the patch projections, wherein the distribution member evenly disperses filling material across the mold surface so that the filling material evenly fills the mold;
   b) filling the cavities with filling material, at least in part by urging filling material from the distribution member into the cavities;
   c) causing the filling material to solidify; and
   d) separating the solidified filling material and the mold to thereby form the patch.
2. The method according to claim 1, wherein the method includes causing filling material on the mold surface to solidify, thereby forming a patch base.
3. The method according to claim 1, wherein the step of providing a distribution member and filling material on the mold surface includes:
   a) providing the distribution member on the mold surface; and
   b) applying the filling material to the distribution member.
4. The method according to claim 1, wherein the distribution member is at least one of:
   a) a diffusion filter; and
   b) a membrane.
5. The method according to claim 1, wherein the method of solidifying the filling material includes at least one of:
   a) exposure to vacuum;
   b) temperature control;
   c) humidity control;
   d) using a gas flow; and
   e) exposing the filling material to a reagent;
   f) exposing the filling material to UV light; and
   g) exposing the filling material to radiation.
6. The method according to claim 1, wherein the method of urging the filling material into the cavities includes using a centrifuge.
7. The method according to claim 1, wherein the step of filling the cavities with filling material includes:
   a) calculating a volume of filling material required to at least partially fill the cavities; and
   b) filling the cavities using the calculated volume of filling material.
8. The method according to claim 1, wherein the method includes forming the projections with at least two layers of filling material.
9. The method according to claim 1, wherein resulting projections include at least two layers.
10. The method according to claim 1, wherein the step of filling the cavities with filling material includes:
    a) partially filling the cavities with a first filling material; and
    b) filling a cavity using at least a second filling material.
11. The method according to claim 10, wherein the method includes filling the cavity using at least a third filling material.
12. The method according to claim 11, wherein the third filling material forms a patch base.
13. The method according to claim 10, wherein the step of partially filling the cavities with the first filling material includes:
    a) determining a layer depth;
    b) calculating a volume of first fluid material in accordance with the layer depth; and
    c) partially filling the cavities using the calculated volume of first filling material.
14. The method according to claim 1, wherein the step of filling the cavities with filling material includes:
    a) urging a first filling material from a first distribution member into the cavities, to thereby partially fill the cavities;
    b) causing the first filling material to solidify;
    c) urging a second filling material from a second distribution member into the cavities, to thereby fill the cavities; and
    d) causing the second filling material to solidify.
15. The method according to claim 14, wherein the step of filling the cavities with filling material further includes:
    a) urging a third filling material from a third distribution member into the cavities, to thereby fill the cavities; and
    b) causing the third filling material to solidify.
16. The method according to claim 14, wherein the method includes replacing the first distribution member with the second distribution member prior to providing the second filling material.
17. The method according to claim 1, wherein the method includes:
    a) prior to providing the filling material on the mold surface, determining mold properties; and
    b) selecting filling material properties at least partially in accordance with the mold properties.
18. The method according to claim 17, wherein the mold properties include at least one of:
    a) cavity size;
    b) cavity shape;
    c) cavity spacing;
    d) cavity surface properties; and
    e) mold materials.
19. The method according to claim 17, wherein the filling material properties include at least one of:
    a) a surface tension; and
    b) a viscosity.
20. The method according to claim 17, wherein the method includes forming a filling material having selected filling material properties, the filling material including at least one of:
    a) a viscosity enhancer;
    b) a detergent;
    c) a surfactant; and
    d) an adjuvant.
21. The method according to claim 1, wherein the filling material is dissolvable on contact with fluid in a subject.
22. The method according to claim 1, wherein the filling material includes a material for delivery to a subject in use.
23. The method according to claim 22, wherein the material is at least one of:
    a) a biological agent; and
    b) a therapeutic agent.
24. The method according to claim 22, wherein the material is at least one of:
    a) nanoparticles;
    b) a nucleic acid or protein;
    c) an antigen, allergen, or adjuvant;
    d) parasites, bacteria, viruses, or virus-like particles;
    e) quantum dots, SERS tags, raman tags or other nanobiosensors;
    f) metals or metallic compounds;
    g) molecules, elements or compounds;

h) DNA;
i) protein;
j) RNA, siRNA, sfRNA, iRNA;
k) synthetic biological materials;
l) polymers; and,
m) drugs.

25. The method according to claim 1, wherein the method includes:
  a) forming the mold prior to providing the distribution member and filling material on the mold surface by creating a male mold having a number of projections; and
  b) using the male mold to thereby form the mold.

26. The method according to claim 25, wherein the method includes creating the male mold using an etching process.

27. The method according to claim 25, wherein the method includes etching a silicon substrate to thereby form the male mold.

28. A method for use in producing a patch having a number of projections thereon, the method including:
  a) providing a first filling material on a mold surface of a mold, the mold including a number of cavities extending from the mold surface for defining the patch projections;
  b) partially filling the cavities with first filling material;
  c) causing the first filling material to solidify;
  d) providing a second filling material on the mold surface;
  e) filling the cavities with second filling material;
  f) causing the second filling material to solidify; and
  g) separating the solidified filling material and the mold to thereby form the patch.

29. The method according to claim 28, wherein the method includes:
  a) providing a first distribution member on the mold surface with the first filling material;
  b) partially filling the cavities with the first filling material, at least in part by urging the first filling material from the first distribution member into the cavities;
  c) providing a second distribution member on the mold surface with the second material; and
  d) filling the cavities with the second filling material, at least in part by urging the second filling material from the second distribution member into the cavities.

* * * * *